US012644110B2

(12) United States Patent
Leung et al.

(10) Patent No.: US 12,644,110 B2
(45) **Date of Patent: *Jun. 2, 2026**

(54) FLUORESCENT BIOSENSOR FOR RAPID DETERMINATION OF L-ARGININE

(71) Applicant: THE HONG KONG POLYTECHNIC UNIVERSITY, Hong Kong (CN)

(72) Inventors: Yun Chung Leung, Hong Kong (CN); Kwok Yin Wong, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 550 days.

This patent is subject to a terminal disclaimer.

(21) Appl. No.: 18/245,005

(22) PCT Filed: Sep. 23, 2021

(86) PCT No.: PCT/CN2021/119920

§ 371 (c)(1),
(2) Date: Mar. 13, 2023

(87) PCT Pub. No.: WO2022/063178

PCT Pub. Date: Mar. 31, 2022

(65) Prior Publication Data

US 2023/0348884 A1 Nov. 2, 2023

Related U.S. Application Data

(60) Provisional application No. 62/706,994, filed on Sep. 23, 2020.

(51) Int. Cl.
*C12N 9/78* (2006.01)
*G01N 33/58* (2006.01)
*G01N 33/68* (2006.01)

(52) U.S. Cl.
CPC ........ *C12N 9/78* (2013.01); *C12Y 305/03006* (2013.01); *G01N 33/582* (2013.01); *G01N 33/6812* (2013.01); *G01N 2333/978* (2013.01)

(58) Field of Classification Search
None
See application file for complete search history.

(56) References Cited

PUBLICATIONS

Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Tam et al. International Journal of Biological Macromolecules, Dec. 15, 2020; 165(Pt A):472-482. (Year: 2020).*
Accession A0A0C6G6L6. Apr. 29, 2015. (Year: 2015).*
Accession A41465. Jun. 30, 1992 (Year: 1992).*

* cited by examiner

*Primary Examiner* — Christian L Fronda
(74) *Attorney, Agent, or Firm* — S&F/WEHRW

(57) ABSTRACT

A recombinant arginine deiminase including a fluorescent group attached via an optional linker to the side chain of a cysteine residue useful for qualitative and quantitative detection of L-arginine in a sample, and methods of use and preparation thereof.

20 Claims, 34 Drawing Sheets

Specification includes a Sequence Listing.

A

A

B

| | **WT-ADI** | **265C** | **265Cf** |
|---|---|---|---|
| $k_{cat}$ ($s^{-1}$) | 30 ± 1 | 20 ± 1 | 16 ± 1 |
| $K_M$ (mM) | 0.03 ± 0.01 | 0.02 ± 0.003 | 0.02 ± 0.001 |
| $k_{cat}/K_M$ ($mM^{-1}s^{-1}$) | 988 ± 272 | 1025 ± 311 | 986 ± 92 |

B

C

D

B

C

A

B

A

B

C

A

B

A

| | 44C | 44Cf |
|---|---|---|
| $k_{cat}$ ($s^{-1}$) | 19 ± 1 | 13 ± 1 |
| $K_M$ (mM) | 0.16 ± 0.08 | 0.10 ± 0.02 |
| $k_{cat}/K_M$ ($mM^{-1}s^{-1}$) | 138 ± 52 | 127 ± 18 |

B

SEQUENCE LISTING

```
<160> NUMBER OF SEQ ID NOS: 10

<210> SEQ ID NO 1
<211> LENGTH: 410
<212> TYPE: PRT
<213> ORGANISM: Artificial Sequence
<220> FEATURE:
<223> OTHER INFORMATION: Arginine Deiminase Cys251 to Ser251 and Thr265
      to Cys265, Synthesized in the lab

<400> SEQUENCE: 1

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205
```

-continued

```
Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Cys Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410


<210> SEQ ID NO 2
<211> LENGTH: 410
<212> TYPE: PRT
<213> ORGANISM: Artificial Sequence
<220> FEATURE:
<223> OTHER INFORMATION: Arginine Deiminase Cys251 to Ser251 and Leu44
      to Cys44, Synthesized in the lab

<400> SEQUENCE: 2

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Cys Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160
```

-continued

```
Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410


<210> SEQ ID NO 3
<211> LENGTH: 410
<212> TYPE: PRT
<213> ORGANISM: Artificial Sequence
<220> FEATURE:
<223> OTHER INFORMATION: Arginine Deiminase Cys251 Blocked and Leu44 to
      Cys44, Synthesized in the lab

<400> SEQUENCE: 3

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Cys Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
```

-continued

```
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410


<210> SEQ ID NO 4
<211> LENGTH: 410
<212> TYPE: PRT
<213> ORGANISM: Artificial Sequence
<220> FEATURE:
<223> OTHER INFORMATION: Arginine Deiminase Cys251 Blocked and Thr265 to
      Cys265, Synthesized in the lab

<400> SEQUENCE: 4

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45
```

-continued

```
Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Cys Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```

<210> SEQ ID NO 5
<211> LENGTH: 33
<212> TYPE: DNA
<213> ORGANISM: Artificial Sequence
<220> FEATURE:
<223> OTHER INFORMATION: Forward primer of C251S, Synthesized in the lab

<400> SEQUENCE: 5

-continued

```
gttgctaata aagaaagcga attcaaacgt att                              33


<210> SEQ ID NO 6
<211> LENGTH: 33
<212> TYPE: DNA
<213> ORGANISM: Artificial Sequence
<220> FEATURE:
<223> OTHER INFORMATION: Reverse primer of C251S, Synthesized in the lab

<400> SEQUENCE: 6

aatacgtttg aattcgcttt ctttattagc aac                              33


<210> SEQ ID NO 7
<211> LENGTH: 54
<212> TYPE: DNA
<213> ORGANISM: Artificial Sequence
<220> FEATURE:
<223> OTHER INFORMATION: Forward primer of 44C, Synthesized in the lab

<400> SEQUENCE: 7

gactatatta caccagctag actagatgaa ttatgcttct cagctatctt agaa       54


<210> SEQ ID NO 8
<211> LENGTH: 51
<212> TYPE: DNA
<213> ORGANISM: Artificial Sequence
<220> FEATURE:
<223> OTHER INFORMATION: Reverse primer of 44C, Synthesized in the lab

<400> SEQUENCE: 8

ttctaagata gctgagaagc attcatctag tctagctggt gtaatatagt c          51


<210> SEQ ID NO 9
<211> LENGTH: 53
<212> TYPE: DNA
<213> ORGANISM: Artificial Sequence
<220> FEATURE:
<223> OTHER INFORMATION: Forward primer of 265C, Synthesized in the lab

<400> SEQUENCE: 9

tgttgcaatt aacgttccaa aatggtgcaa cttaatgcac ttagacacat ggc        53


<210> SEQ ID NO 10
<211> LENGTH: 53
<212> TYPE: DNA
<213> ORGANISM: Artificial Sequence
<220> FEATURE:
<223> OTHER INFORMATION: Reverse primer of 265C, Synthesized in the lab

<400> SEQUENCE: 10

gccatgtgtc taagtgcatt aagttgcacc attttggaac gttaattgca aca        53
```

FLUORESCENT BIOSENSOR FOR RAPID DETERMINATION OF L-ARGININE

CROSS-REFERENCE TO RELATED APPLICATIONS

This application claims priority from U.S. Provisional Patent Application No. 62/706,994 filed on Sep. 23, 2020, the content of which is hereby incorporated by reference in its entirety.

TECHNICAL FIELD

The present disclosure generally relates to fluorescent recombinant proteins useful in the quantitative and qualitative detection of L-arginine (L-Arg) in a sample, intermediates thereof, and methods of use and preparation thereof. More particularly, the present disclosure relates to a fluorescent recombinant arginine deiminase (ADI), intermediates thereof, and methods of use and preparation thereof.

BACKGROUND

L-Arg is considered a miracle molecule by many due to the significant roles it plays in acting as precursor and anti-aggregating agent of numerous proteins and molecules for metabolism. Its concentration in a subject can be an indicator of the degree of healthiness of the subject and its concentration in food can be an indicator of the quality of the food.

Generally, the normal L-Arg concentration in humans is about 100-120 μM. This range can be a kind of references of physiological conditions since elevated plasma L-Arg concentration has been observed in some arginase deficiency persons whilst low L-Arg concentrations have been found in L-Arg auxotrophic cancer patients. On the other hand, measurement of plasma L-Arg concentrations is one of the key parameters that reflects the potency of arginine-depleting drugs for the treatment of cancers and other diseases.

In the area of food processing, L-Arg is an index for monitoring the safety of beverages, especially in wine production. During the fermentation process, L-Arg is converted into urea, which is accumulated and sequentially reacts with ethanol to produce a hazardous and carcinogenic compound, ethyl carbamate. Therefore, the monitoring of L-Arg concentrations in clinical, biological and food samples is fundamentally important.

There are numerous methods to detect L-Arg concentrations, such as ionization mass spectrometry and high-performance liquid chromatography to provide accurate quantitative analyses, but they involve high operating costs and long measurement times. Biosensors, on the other hand, can provide fast response and high specificity for determination of analytes, and thus, they are commonly used in drug discovery, diagnosis, and food safety and processing. Different types of L-Arg biosensors have been developed and they exhibit wide linear detection ranges with rapid response time. Details of their characteristics are summarized in Table 1. However, these biosensors have the following disadvantages: (a) the specificity of biosensor is poor due to the use of ammonium ($NH_3$) as a proxy analyte for L-Arg. An additional measurement of $NH_3$ concentration is thus required for samples that contain $NH_3$, (b) Two enzymes system (arginase/urease) can introduce greater error than one enzyme systems in the detection of L-Arg.

There is thus a need for improved L-Arg biosensors that address or overcome one or more of the aforementioned disadvantages.

SUMMARY

The present disclosure provides fluorescent biosensors comprising a fluorescent recombinant protein that can be used in the direct detection and/or measurement of L-Arg in a sample. The fluorescent recombinant proteins described herein can be bio-engineered for site-specific attachment of a fluorophore, such as fluorescein-5-maleimide (F5M). The incorporation of F5M into the recombinant protein results in the generation of fluorescence intensity changes upon the binding of L-Arg with the recombinant protein, showing a high specificity of the biosensor. The fluorescent biosensors can accurately detect and/or measure L-Arg concentration in a sample, such as an animal serum (e.g. fetal bovine serum), a result that is quantitative and comparable with the results determined by sophisticated mass-spectrometry. Therefore, the compositions and methods described herein provided a simple method for rapid and accurate determination of L-Arg concentrations in biological or complicated samples.

In a first aspect, provided herein is a recombinant arginine deiminase (ADI) comprising a polypeptide having at least 95% sequence homology with a polypeptide sequence selected from the group consisting of SEQ ID NO: 1 and SEQ ID NO: 2, wherein the amino acid at position 251 of SEQ ID NO: 1 is not cysteine; and the amino acid at position 265 of SEQ ID NO: 1 must be cysteine; and the amino acid at position 44 of SEQ ID NO: 2 must be cysteine; and the amino acid at position 251 of SEQ ID NO: 2 is not cysteine.

In certain embodiments, the amino acid at position 251 of SEQ ID NO: 1 must be serine; and the amino acid at position 251 of SEQ ID NO: 2 must be serine.

T In certain embodiments, the polypeptide has at least 97.5% sequence homology with the polypeptide sequence selected from the group consisting of SEQ ID NO: 1 and SEQ ID NO: 2.

In certain embodiments, the polypeptide has at least 98.7% sequence homology with the polypeptide sequence selected from the group consisting of SEQ ID NO: 1 and SEQ ID NO: 2.

In certain embodiments, the recombinant ADI consists of SEQ ID NO: 1 or SEQ ID NO: 2.

In a second aspect provided herein is a fluorescent recombinant ADI comprising the recombinant ADI of the first aspect and a fluorescent dye covalently attached via an optional linker to the side chain of the cysteine at position 265 of SEQ ID NO: 1 or to the side chain of the cysteine at position 44 of SEQ ID NO: 2.

In certain embodiments, the fluorescent dye comprises a fluorescein derivative, a BODIPY derivative, an eosin derivative, a rhodamine derivative, a PyMPO derivative, a benzoxadiazole derivative, or a Lucifer yellow derivative.

In certain embodiments, the fluorescent dye is attached via a linker comprising a 2,5-dioxopyrrolidin-3-yl moiety, an acetyl moiety, or an ethylene moiety to the side chain of the cysteine at position 265 of SEQ ID NO: 1 or to the side chain of the cysteine at position 44 of SEQ ID NO: 2.

In certain embodiments, the fluorescent dye and linker is fluorescein-5-(2,5-dioxopyrrolidin-3-yl).

In a third aspect provided herein is a method of detecting L-arginine (L-Arg) in a sample suspected of containing L-Arg, the method comprising: contacting the fluorescent recombinant ADI of the second aspect with the sample and measuring the fluorescence of the fluorescent recombinant ADI.

In certain embodiments, the fluorescent recombinant ADI consists of SEQ ID NO: 1 or SEQ ID NO: 2.

In certain embodiments, the fluorescent dye is a fluorescein derivative, a BODIPY derivative, an eosin derivative, a rhodamine derivative, a PyMPO derivative, a benzoxadiazole derivative, or a Lucifer yellow derivative; and the fluorescent dye is attached via a linker comprising a N-succinimidyl (2,5-dioxopyrrolidin-3-yl) moiety, an acetyl moiety, or an ethylene moiety to linker to the side chain of the cysteine at position 265 of SEQ ID NO: 1 or to the side chain of the cysteine at position 44 of SEQ ID NO: 2.

In certain embodiments, the fluorescent dye and linker is fluorescein-5-N-succinimidyl, 6-acetamidofluorescein (6-iaf), tetramethylrhodamine-5-N-succinimidyl (T5M), or 6-acetyl-2-dimethylaminonaphthalene (BADAN).

In certain embodiments, the method further comprises the step of determining the concentration of L-Arg in the sample based on the measured fluorescence of the fluorescent recombinant ADI.

In certain embodiments, the step of measuring the fluorescence of the fluorescent recombinant ADI comprises measuring the time at the maximum rate of the fluorescence change of the fluorescent recombinant ADI in the sample.

In certain embodiments, the step of determining the concentration of L-Arg in the sample comprises comparing the measured time at the maximum rate of the fluorescence change of the fluorescent recombinant ADI in the sample to one or more calibration curves prepared by using the interrelation between known concentrations of L-Arg in standard samples comprising the fluorescent recombinant ADI and the time at the maximum rate of the fluorescence change of the fluorescent recombinant ADI in the standard samples; and determining the concentration of L-Arg in the sample.

In certain embodiments, the method has a linear detection range of 2.5 to 100 μM L-Arg in the sample.

In certain embodiments, the time required from the step of contacting the recombinant ADI and the sample to measuring the fluorescence of the recombinant ADI is between 0.15-4 minutes.

In certain embodiments, the sample is a biological sample.

In a fourth aspect, provided herein is a method of preparing the fluorescent recombinant ADI of the second aspect, the method comprising: contacting a recombinant ADI with a reactive fluorescent dye reagent comprising a fluorescent dye covalently bonded via an optional linker to a reactive moiety selected from the group consisting of maleimide moiety, an acetyl halide, and an ethylene halide thereby forming the fluorescent recombinant ADI, wherein the recombinant ADI comprises a polypeptide having at least 95% sequence homology with a polypeptide sequence selected from the group consisting of SEQ ID NO: 1 and SEQ ID NO: 2, wherein the amino acid at position 251 of SEQ ID NO: 1 is not cysteine; and the amino acid at position 265 of SEQ ID NO: 1 must be cysteine; and the amino acid at position 44 of SEQ ID NO: 2 must be cysteine; and the amino acid at position 251 of SEQ ID NO: 2 is not cysteine In certain embodiment, the reactive fluorescent dye reagent is fluorescein-5-maleimide, 6-iodoacetamidofluorescein (6-iaf), tetramethylrhodamine-5-maleimide (T5M), or 6-bromoacetyl-2-dimethylaminonaphthalene (BADAN).

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Definitions

Figure 1:
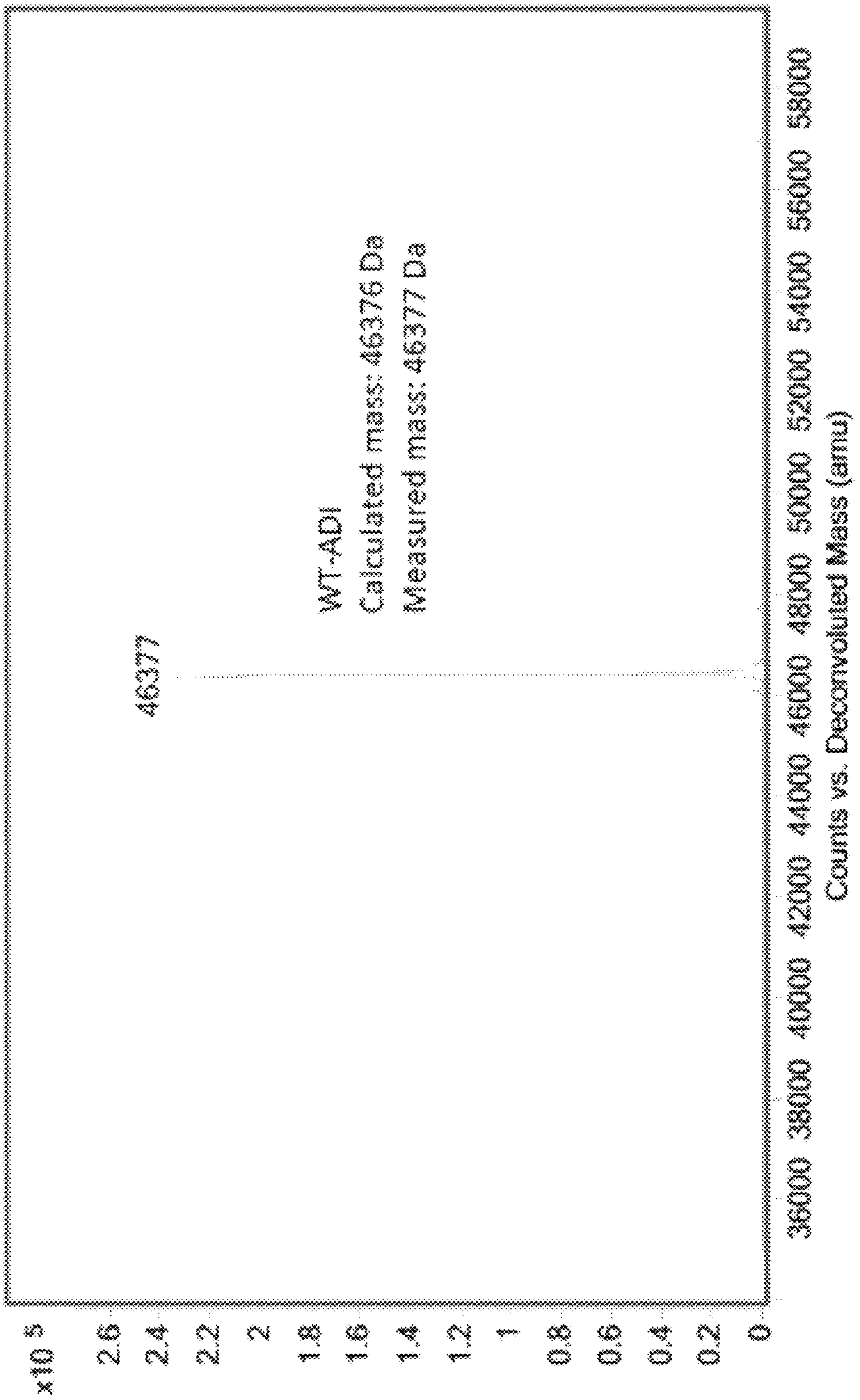
FIG. 1 depicts ESI-MS spectra of different arginine deiminases:—(A) Wild type arginine deiminase (WT-ADI); (B) 265C; and (C) 265Cf.
Figure 1:
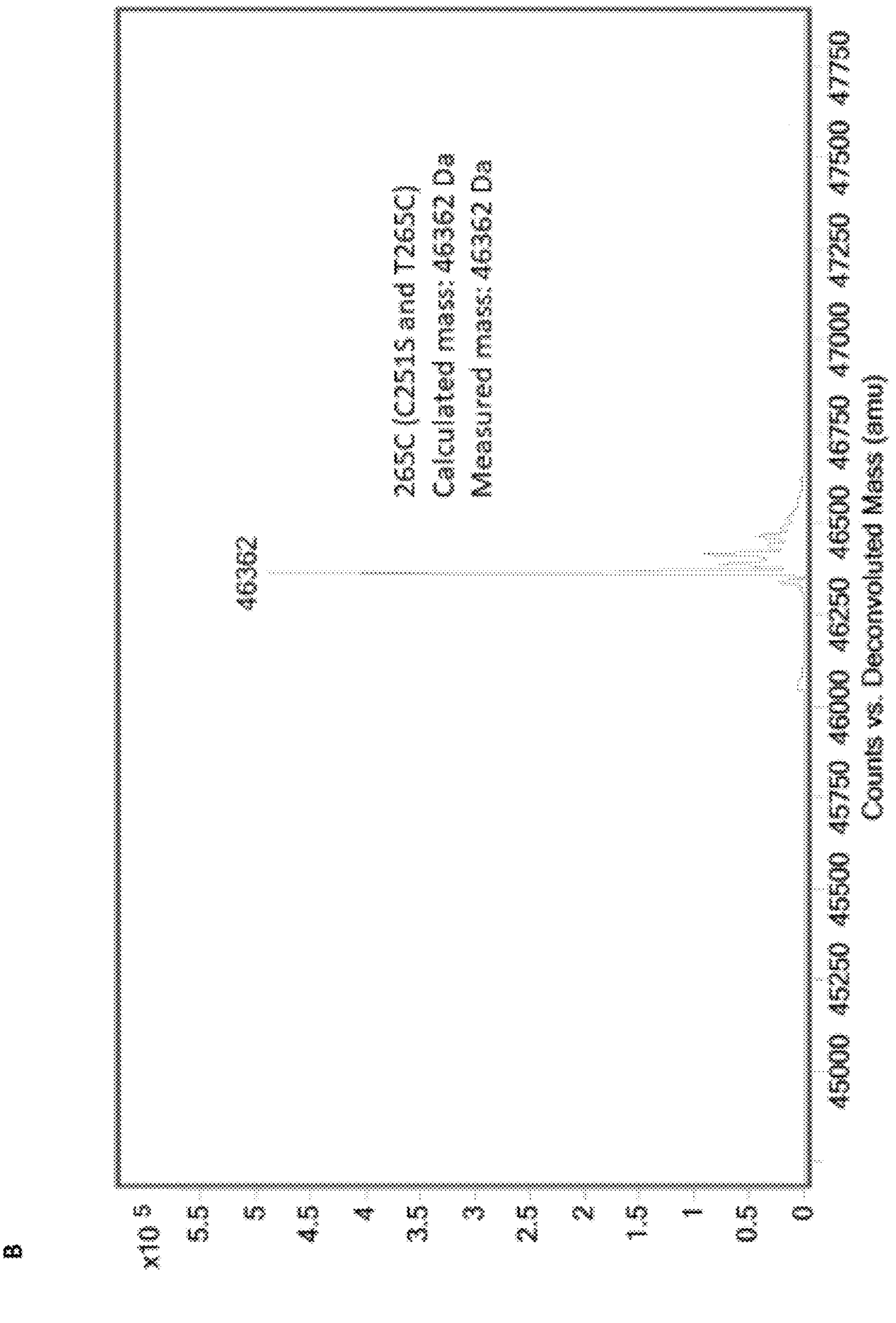
Figure 1:
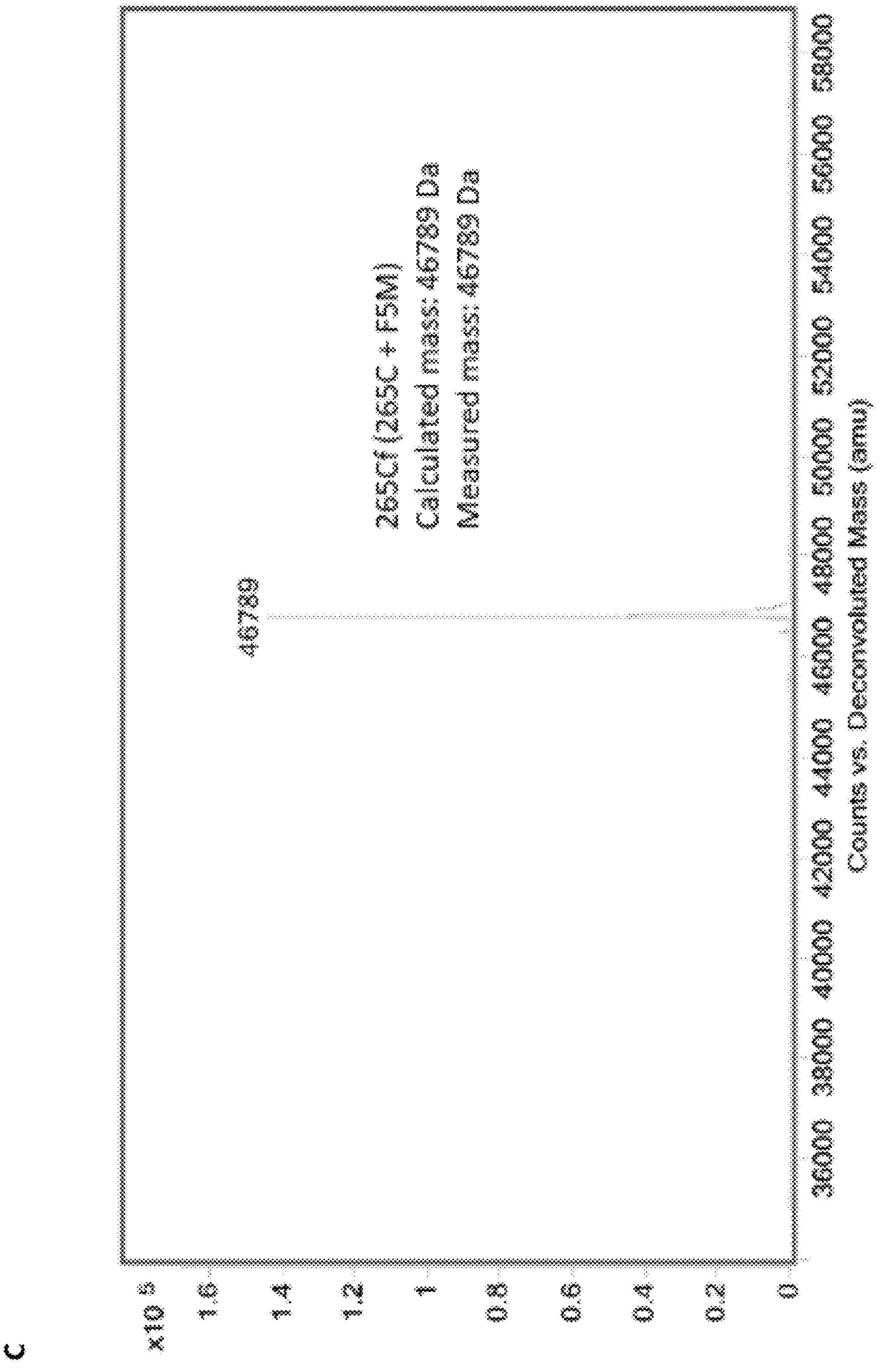

As used herein, the term "variant" refers to a polypeptide or sequence differing from a reference polypeptide or polynucleotide sequence, but retaining essential properties thereof. Generally, variants are overall closely similar, and, in many regions, identical to the reference polypeptide or polynucleotide sequence.

A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

The term "amino acid modification" as used herein indicates amino acid insertion, substitution, or deletion, etc. Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The term "percentage sequence homology", when used in reference to a polypeptide or polynucleotide sequence, refers to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions for the longer sequence in the window of comparison and multiplying the result by 100 to yield the percentage of sequence homology. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

The terms "fluorescent dye", "fluorophore", or the like refer interchangeably to molecules, groups or radicals that are fluorescent. The term "fluorescent" as applied to a molecule or compound is used to refer to the property of the compound of absorbing energy (such as UV, visible or IR radiation) and re-emitting at least a fraction of that energy as light over time. Fluorescent dyes include, but are not limited to small molecules, proteins and macromolecular complexes.

The term "composition" is intended to encompass a product comprising the specified ingredients in the specified amounts, as well as any product that results, directly or indirectly, from combinations of the specified ingredients in the specified amounts.

The term "sample" as used herein relates to a material or mixture of materials, typically, although not necessarily, in fluid form, but can also be in solid or gaseous form, suspected of containing L-Arg. In certain embodiments, the sample are derived from a variety of sources, such as from food stuffs, environmental materials (e.g., soil, air, water, and the like), or a biological such as a body fluid, a sample from a tissue or an organ, or a sample of wash/rinse fluid or a swab or smear obtained from an outer or inner body surface. In certain embodiments, samples of stool, urine, saliva, cerebrospinal fluid, blood, serum, plasma, or lacrimal fluid are encompassed as samples by the methods described herein.

As used herein, the term "subject" refers to any animal (e.g., a mammal), including, but not limited to, humans, non-human primates, canines, felines, and rodents.

Provided herein is a recombinant ADI, wherein the recombinant ADI contains no more than one cysteine residue, wherein the no more than one cysteine residue further comprises a fluorescent dye covalently bonded to its side chain via an optional linker.

The recombinant ADI can be any ADI known in the art, such as those produced from *Mycoplasma, Lactococcus, Pseudomonas, Steptococcus, Escherichia, Mycobacterium* or *Bacillus* microorganisms. Exemplary arginine deiminase include, but are not limited, to those produced by *Mycoplasma hominis, Mycoplasma arginini, Mycoplasma arthritidis, Clostridium perfringens, Bacillus licheniformis, Borrelia burgdorferi, Borrelia afzellii, Enterococcus faecalis, Lactococcus lactis, Bacillus cereus, Streptococcus pyogenes, Steptococcus pneumoniae, Lactobacillus sake, Giardia intestinalis, Mycobacterium tuberculosis, Pseudomonas plecoglossicida, Pseudomonas putida, Pseudomonas aeruginosa*, and the like, and variants thereof. In certain embodiments, the recombinant ADI is *Mycoplasma arginine* or a variant thereof.

The recombinant ADI can be the full protein or a functional fragment and/or variant thereof.

Methods for preparing variants of a recombinant ADI which contains no more than one cysteine residue are well known in the art. A person of ordinary skill in the art could readily select the site of the cysteine residue in the recombinant ADI and prepare it using the methods described herein and well known techniques.

In certain embodiments, the recombinant ADI comprises a polypeptide having at least 95% sequence homology with a polypeptide sequence selected from the group consisting of SEQ ID NO: 1 and SEQ ID NO: 2, wherein the amino acid at position 251 of SEQ ID NO: 1 is not cysteine; and the amino acid at position 265 of SEQ ID NO: 1 must be cysteine; and the amino acid at position 44 of SEQ ID NO: 2 must be cysteine; and the amino acid at position 251 of SEQ ID NO: 2 is not cysteine.

In certain embodiments, the amino acid at position 251 of SEQ ID NO: 1 is selected from the group consisting of ala, arg, asn, asp, glu, gln, gly, his, ile, leu, lys, met, phe, pro, ser, thr, trp, tyr, and val. In certain embodiments, the amino acid at position 251 of SEQ ID NO: 1 is selected from the group consisting of ala, gly, ile, leu, met, ser, thr, and val. In certain embodiments, the amino acid at position 251 of SEQ ID NO: 1 is ser, leu, val, gly, and ala. In certain embodiments, the amino acid at position 251 of SEQ ID NO: 1 is ser.

In certain embodiments, the amino acid at position 44 of SEQ ID NO: 2 is selected from the group consisting of ala, arg, asn, asp, glu, gln, gly, his, ile, leu, lys, met, phe, pro, ser, thr, trp, tyr, and val. In certain embodiments, the amino acid at position 44 of SEQ ID NO: 2 is selected from the group consisting of ala, gly, ile, leu, met, ser, thr, and val. In certain embodiments, the amino acid at position 44 of SEQ ID NO: 2 is ser, leu, val, gly, and ala. In certain embodiments, the amino acid at position 44 of SEQ ID NO: 2 is ser.

In certain embodiments, the recombinant ADI comprises a polypeptide having at least 95% sequence homology with a polypeptide sequence selected from the group consisting of SEQ ID NO: 1 and SEQ ID NO: 2, wherein the amino acid at position 251 of SEQ ID NO: 1 must be serine; and the amino acid at position 265 of SEQ ID NO: 1 must be cysteine; and the amino acid at position 44 of SEQ ID NO: 2 must be cysteine; and the amino acid at position 251 of SEQ ID NO: 2 must be serine.

In certain embodiments, the recombinant ADI contains no more than one cysteine residue.

In certain embodiments, the recombinant ADI comprises a polypeptide having at least 96.3%, 97.5%, 97.8%, 98.0%, 98.3%, 98.5%, 98.8%, 99.0%, 99.3%, 99.5%, or 99.7% sequence homology with the polypeptide sequence selected from the group consisting of SEQ ID NO: 1 and SEQ ID NO: 2.

In certain embodiments, the recombinant ADI consists of a polypeptide having at least 96.3%, 97.5%, 97.8%, 98.0%, 98.3%, 98.5%, 98.8%, 99.0%, 99.3%, 99.5%, or 99.7% sequence homology with the polypeptide sequence selected from the group consisting of SEQ ID NO: 1 and SEQ ID NO: 2.

In certain embodiments, the variants of SEQ ID NO: 1 and SEQ ID NO: 2 having the sequence homologies described herein include only conservative amino acid substitutions relative to SEQ ID NO: 1 and SEQ ID NO: 2.

In certain embodiments, the recombinant ADI consists of a polypeptide having 100% sequence homology with SEQ ID NO: 1 or SEQ ID NO: 2.

The present disclosure also provides a fluorescent recombinant ADI comprising a recombinant ADI as described herein further comprising a fluorescent dye covalently bonded via an optional linker to the side chain of the cysteine residue at position 265 of SEQ ID NO: 1; or to the side chain of the cysteine residue at position 44 of SEQ ID NO: 2.

The fluorescent dye can be a fluorescein derivative, a BODIPY derivative, an eosin derivative, a rhodamine derivative, a PyMPO derivative, a benzoxadiazole derivative, or a Lucifer yellow derivative.

In certain embodiments, the fluorescent dye has the Formula I:

I

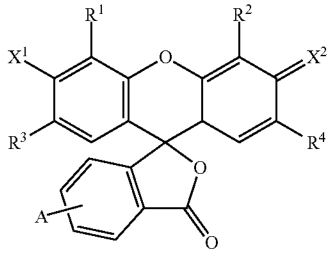

or a conjugate salt and/or tautomer thereof, wherein

- $X^1$ is Oh and $X^2$ is O; or $X^1$ is $N(Me)_2$ and $X^2$ is $N(Me)_2^+$;
- each of $R^1$, $R^2$, $R^3$, and $R^4$ is independently hydrogen, chloride, bromide, or methyl; and
- A represents the site of attachment of the fluorescent recombinant ADI via an optional linker.

In certain embodiments, the linker is selected from the group consisting of:

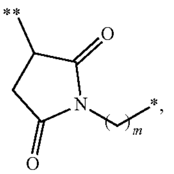
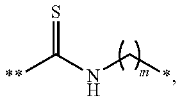
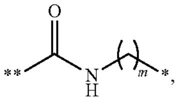
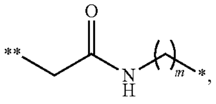
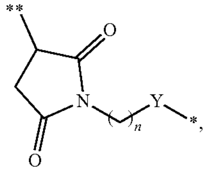
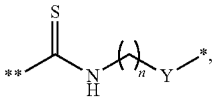
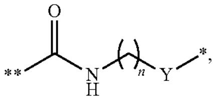
and
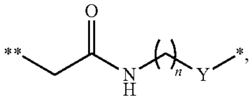

wherein:

- m is a whole number selected from 0-6;
- n is a whole number selected from 2-6;
- Y is —O—, —(NH)—, —C═O—, —C═ONH—, —C═OO—, —NHC═O—, or —OC═O—;
- * represents the site of attachment of the fluorescent dye of Formula I; and
- ** represents the site of attachment of the fluorescent recombinant ADI.

In certain embodiments, the fluorescent dye and linker have the Formula II:

II

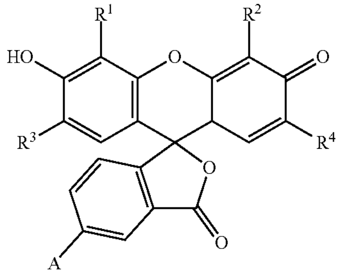

or a conjugate salt and/or tautomer thereof, wherein

- each of $R^1$, $R^2$, $R^3$, and $R^4$ is independently hydrogen, chloride, bromide, or methyl; and
- A is selected from the group consisting of:

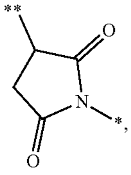
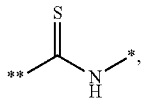
and
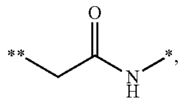

wherein * represents the site of attachment of the fluorescent dye of Formula II; and

- ** represents the site of attachment of the fluorescent recombinant ADI.

In certain embodiments, $R^1$, $R^2$, $R^3$, and $R^4$ are hydrogen; $R^1$, $R^2$, $R^3$, and $R^4$ are bromide; or $R^1$ and $R^2$ are methyl; and $R^3$ and $R^4$ are iodide.

In certain embodiments, the fluorescent dye and linker are selected from the group consisting of:

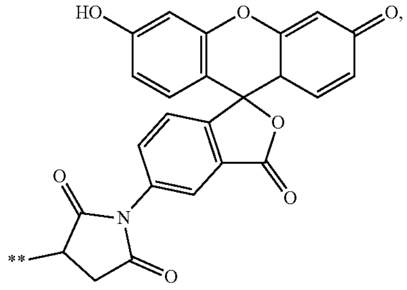
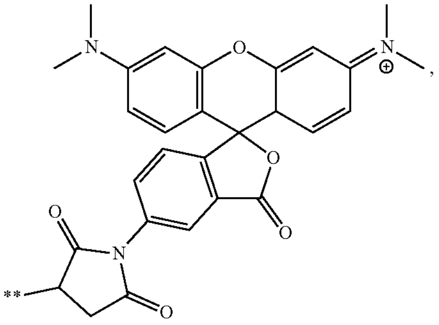

-continued

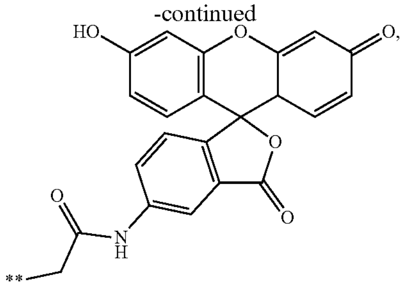

,

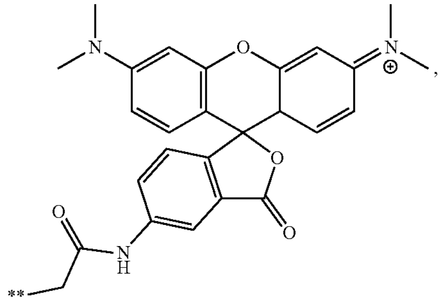

,

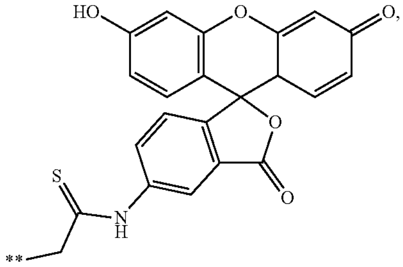

,

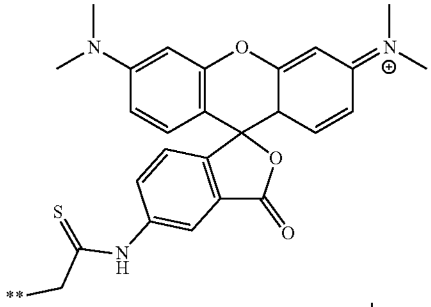

, and

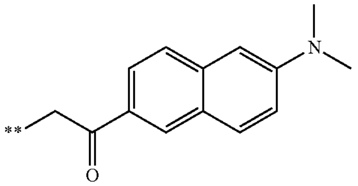

, wherein ** represents the site of attachment of the fluorescent recombinant ADI.

The fluorescent recombinant ADI can be prepared by reacting the recombinant ADI with a reactive fluorescent dye reagent selected from the group consisting of Alexa Fluor® 488 (A10254[M]), Alexa Fluor® 532 (A10255), Alexa Fluor® 546 (A10258[M]), Alexa Fluor® 555 (A20346), Alexa Fluor® 568 (A20341[M]), Alexa Fluor® 594 (A10256[M]), Alexa Fluor® 633 (A20342[M]), Alexa Fluor® 647 (A20347), Alexa Fluor® 660 (A20343), Alexa Fluor® 680 (A20344), Alexa Fluor® 750 (A30459), BODIPY® FL (B10250, D6003), BODIPY® TMR (B30466), BODIPY® TR, BODIPY® 493/503 (B2103), BODIPY® 499/508 (D20350), BODIPY® 507/545 (D6004)), BODIPY® 577/618 (D20351), BODIPY® 630/650 (B22802), Oregon Green® 488 (O6034[5], O6010[M]), 4-dimethylamino phenylazophenyl (D1521), eosin (E118[5]), fluorescein (F150[5], I30451[5], I30452[6]), Lucifer yellow (L1338), NBD (I9, D2004), PyMPO (06034[5], 06010[M]), QSY® 7 (Q10257), QSY® 9 (Q30457), QSY® 35 (Q2034B), Rhodamine Red™ (R6029[M]), sulfonerhodamine (B10621), tetramethylrhodamine (T6027[5], T6028[6], T6006[5]), and Texas Red® (T6008[M], T6009[M]); resulting in the alkylation of the side chain of the cysteine residue at position 265 of SEQ ID NO: 1; or the side chain of the cysteine residue at position 44 of SEQ ID NO: 2 with the fluorescent dye. The fluorescent dyes can also include Fluorescein-5-maleimide (F5M), 6-iodoacetamidofluorescein (6-iaf), Tetramethylrhodamine-5-maleimide (T5M), 6-bromoacetyl-2-dimethylaminonaphthalene (BADAN), Alexa 488 (blue), Cy3b (green), Alexa 647 (red). For labeling thiol groups, there are thiol-reactive Alexa Fluor® dyes that span the visible spectrum, including Alexa Fluor® 350 C5-maleimide (A30505), Alexa Fluor® 488 C5-maleimide (A10254), Alexa Fluor® 532 C5-maleimide (A10255), Alexa Fluor® 546 C5-maleimide (A10258), Alexa Fluor® 555 C2 maleimide (A20346), Alexa Fluor® 568 C5-maleimide (A20341), Alexa Fluor® 594 C5-maleimide (A10256), Alexa Fluor® 633 C5-maleimide (A20342), Alexa Fluor® 647 C2-maleimide (A20347), Alexa Fluor® 660 C2-maleimide (A20343), Alexa Fluor® 680 C2-maleimide (A20344), Alexa Fluor® 750 C5-maleimide (A30459).

In alternative embodiments, provided herein is a fluorescent recombinant protein comprising a recombinant protein selected from the group consisting of ADI, arginase, arginine decarboxylase, and arginine 2 monooxygenase and a fluorescent dye covalently bonded via an optional linker to the side chain of a cysteine residue in the recombinant protein, wherein the recombinant protein comprises no more than one cysteine residue and the fluorescent dye and optional linker are each independently as described herein.

The arginase can be any arginase known in the art, such as those produced by bacteria, fungi, fish, human, bovine, swine, rabbit, rodent, primate, sheep and goat. For example, *Bacillus caldovelox* arginase, *Thermus thermophilus* arginase, *Capra hircus* arginase I, *Heterocephalus glaber* arginase I, *Bos taurus* arginase I, *Sus scrofa* arginase I, *Plecoglossus altivelis* arginase I, *Salmo salar* arginase I, *Oncorhynchus mykiss* arginase I, *Osmerus mordax* arginase I, *Hyriopsis cumingii* arginase I, *Rattus norvegicus* arginase I, *Mus musculus* arginase I, *Homo sapiens* (human) arginase I, *Pan troglodytes* arginase I, *Oryctolagus cuniculus* arginase I, *Rattus norvegicus* arginase II, *Mus musculus* arginase II, *Homo sapiens* (human) arginase II, *Bostaurus* arginase II, *Heterocephalus glaber* arginase II, *Pan troglodytes* arginase II, *Oryctolagus cuniculus* arginase II, *Delftia* arginase, *Bacillus coagulans* arginase, *Hoeflea phototrophica* arginase and *Roseiflexus castenholzii* arginase. Other examples include arginases from *Bacillus methanolicus*, *Bacillus* sp. NRRL B-14911, *Planococcus donghaensis*, *Paenibacillus dendritiformis*, *Desmospora* sp., *Methylobacter tundripaludum*, *Stenotrophomonas* sp., *Microbacterium laevaniformans*, *Porphyromonas uenonis*, *Agrobacterium* sp., *Octadecabacter arcticus*, *Agrobacterium tumefaciens*, *Anoxybacillus flavithermus*, *Bacillus pumilus*, *Geobacillus thermoglucosidasius*, *Geobacillus thermoglucosidans*, *Brevibacillus laterosporus*, *Desulfotomaculum ruminis*, *Geobacillus kaustophilus*, *Geobacillus thermoleovorans*, *Geobacillus thermodenitrificans*, *Staphylococcus aureus*, *Halophilic archaeon* DL31, *Halopigerxanaduensis*, *Natrialba magadii*, *Plasmodium falciparum*, *Helicobacter pylori*, and the like, and variants thereof.

The arginine decarboxylase can be any arginine decarboxylase known in the art, such as those produced by *Escherichia coli., Salmonella typhimurium, Chlamydophila pneumoniae, Methanocaldococcus jannaschii, Paramecium bursaria Chlorella* virus 1, *Vibrio vulnificus* YJ016, *Campylobacter jejuni* subsp., *Trypanosoma cruzi, Sulfolobus solfataricus, Bacillus licheniformis, Bacillus cereus, Carica papaya, Nicotianatobacum, Glycine max, Lotus coniculata, Vibrio vulnificus, Vibrio cholerae, Mus musculus, Thermotoga, Rattus norvegicus, Homo sapiens, Bos taurus, Sus scrofa, Thermus thermophiles, Thermus parvatiensis, Thermus aquaticus, Thermus thermophilus, Thermus islandicus, Arabidopsis thaliana, Avena sativa*, and the like and variants thereof.

The arginine 2-monooxygenase can be any arginine 2-monooxygenase known in the art, such as those produced from *Arthrobacter globiformis* IFO 12137, *Arthrobacter simplex* IFO 12069, *Brevibacterium helvolum* IFO 12073, *Helicobacter cinaedi* CCUG 18818, *Streptomyces griseus*, and the like and variants thereof.

The arginine decarboxylase, arginine deiminase, arginine 2-mono-oxygenase, and arginase can be the full protein or a functional fragment and/or variant thereof.

The present disclosure also provides a method of detecting L-Arg in a sample suspected of containing L-Arg, the method comprising: contacting the fluorescent recombinant ADI described herein with the sample and measuring the fluorescence of the fluorescent recombinant ADI.

The step of measuring the fluorescence can comprise irradiating the sample with electromagnetic radiation and measuring the luminescence of the fluorescent recombinant ADI. The wavelength of electromagnetic radiation used to irradiate the sample and the wavelength the luminescence is measured at can depend on the selection of the fluorescent dye, but are generally between 250-750 nm. The electromagnetic radiation can have an excitation wavelength between 250-700 nm; 400-600 nm; 400-650 nm; 450-600 nm; 450-550 nm; 475-525 nm; 485-515 nm; 490-510 nm; or 490-500 nm. The luminescence can have an emission wavelength between 300-750 nm; 450-600 nm; 500-600 nm; 500-550 nm; 500-525 nm; or 510-520 nm. Any suitable means for detecting the luminescence can be used, such as a spectrometer.

The method may further comprise the step of determining the concentration of L-Arg in the sample based on the measured fluorescence of the fluorescent recombinant ADI in the sample. In certain embodiments, the step of determining the concentration of L-Arg in the sample based on the measured fluorescence of the fluorescent recombinant ADI in the sample comprises measuring the time at the maximum rate of the fluorescence change of the fluorescent recombinant ADI in the sample.

The step of determining the concentration of L-Arg in the sample can comprise comparing the measured time at the maximum rate of the fluorescence change of the fluorescent recombinant ADI in the sample to one or more calibration curves prepared by using the interrelation between known concentrations of L-Arg in standard samples comprising the fluorescent recombinant ADI and the time at the maximum rate of the fluorescence change of the fluorescent recombinant ADI in the standard samples; and determining the concentration of L-Arg in the sample.

The fluorescence of the fluorescent recombinant ADI can be quenched by 0.0001% to 100% in the sample relative to the fluorescence of the fluorescent recombinant ADI in a sample matrix in the absence of L-Arg or in a standard sample matrix in the absence of L-Arg. In certain embodiments, the fluorescence of the fluorescent recombinant ADI can be quenched by at least 0.01%, at least 0.1%, at least 1%, at least 5%, at least 10%, at least 20%, at least 30%, at least 40%, at least 50%, at least 60%, at least 70%, at least 80%, at least 90%, at least 95%, at least 97%, at least 98%, at least 99%, or 100% relative to the fluorescence of the fluorescent recombinant ADI in the sample matrix in the absence of L-Arg.

The method described herein can have a linear detection range between about 2.5-100 μM.

The sample can be derived from food stuff or a biological sample obtained from a subject, wherein the biological sample is a stool, urine, saliva, cerebrospinal fluid, blood, serum, plasma, or lacrimal fluid. The subject can be any animal including, but not limited to, humans, non-human primates, domesticated animals (e.g., cats, dogs, etc.), livestock (e.g., cattle, horses, pigs, sheep, goats, etc.), laboratory animals (e.g., mouse, rabbit, rat, guinea pig, etc.), and birds In alternative embodiments, the recombinant ADI comprises a polypeptide having at least 95% sequence homology with a polypeptide sequence selected from the group consisting of SEQ ID NO: 3 and SEQ ID NO: 4, wherein the cysteine at position 251 of SEQ ID NO: 3 and SEQ ID NO: 4 is blocked with a thiol blocker; and the amino acid at position 265 of SEQ ID NO: 4 must be cysteine and the amino acid at position 44 of SEQ ID NO: 3 must be cysteine.

In certain embodiments, the ADI comprises a polypeptide having at least 96.3%, 97.5%, 97.8%, 98.0%, 98.3%, 98.5%, 98.8%, 99.0%, 99.3%, 99.5%, or 99.7% sequence homology with a polypeptide sequence selected from the group consisting of SEQ ID NO: 3 and SEQ ID NO: 4.

In certain embodiments, the recombinant ADI consists of a polypeptide having at least 96.3%, 97.5%, 97.8%, 98.0%, 98.3%, 98.5%, 98.8%, 99.0%, 99.3%, 99.5%, or 99.7% sequence homology with a polypeptide sequence selected from the group consisting of SEQ ID NO: 3 and SEQ ID NO: 4.

In certain embodiments, the variants of SEQ ID NO: 3 and SEQ IDO NO: 4 having the sequence homologies described herein include only conservative amino acid substitutions relative to SEQ ID NO: 3 and SEQ ID NO: 4.

In certain embodiments, the cysteine at position 251 of SEQ ID NO: 3 and SEQ ID NO: 4 is blocked with an alpha halo acetamide, such as iodoacetamide, an N-alkyl maleimide, such as N-ethylmaleimide, or an alkyl alkylthiosulfonate, such as methyl methanethiosulfonate.

In certain embodiments, the recombinant ADI comprises a polypeptide having SEQ ID NO: 3, wherein the cysteine at position 251 of SEQ ID NO: 3 is blocked with iodoacetamide and the amino acid at position 44 of SEQ ID NO: 3 must be cysteine.

In certain embodiments, the recombinant ADI comprises a polypeptide having SEQ ID NO: 4, wherein the cysteine at position 251 of SEQ ID NO: 4 is blocked with iodoacetamide and the amino acid at position 265 of SEQ ID NO: 4 must be cysteine.

The present disclosure also provides a fluorescent recombinant ADI comprising a recombinant ADI as described herein further comprising a fluorescent dye covalently bonded via an optional linker to the side chain of the cysteine residue at position 265 of SEQ ID NO: 4; or to the side chain of the cysteine residue at position 44 of SEQ ID NO: 3.

The fluorescent recombinant ADI comprising SEQ ID NO: 3 and SEQ ID NO: 4 may comprise an optional linker as described herein.

The fluorescent recombinant ADI comprising SEQ ID NO: 3 and SEQ ID NO: 4 may comprise a fluorescent dye as described herein.

Provided herein is a fluorescent biosensor (265Cf) that provides a new method for the rapid and specific determination of L-Arg (L-Arg). One of the main features of our biosensor is the high specificity. Existing developed L-Arg biosensors utilize immobilized enzymes, such as arginases, ureases, and arginine deiminases to generate ammonium for analysis. The ability of ammonium to generate potential and pH differences renders it to become analytes. However, this reduces the specificity of the biosensors since side products may be already present in samples to interfere with the detection results. For example, the presence of urea in biological samples can also be hydrolysed by ureases to produce ammonium for detection, which leads to overestimation of L-Arg concentrations. To obtain an accurate detection of the amount of L-Arg in samples, corrections need to be done to eliminate interfering signals. Unlike other L-Arg biosensors, we made use of the specificity of arginine deiminase (ADI) and directly measured L-Arg by using a fluorescent dye attached on the enzyme. The fluorescent dye (fluorescein-5-malemide, F5M) sensed changes in the local environmental, which were the conformational changes of ADI upon L-Arg binding, to generate changes in fluorescence intensity for quantitative analysis. Another unique feature of our biosensor was the simplicity of the manufacturing process. To fabricate our biosensor, only two steps were required, which were the production of ADI mutant and the labelling process. The process was relatively simplified and time-efficient than the manufacturing processes of existing biosensors.

Figure 4:
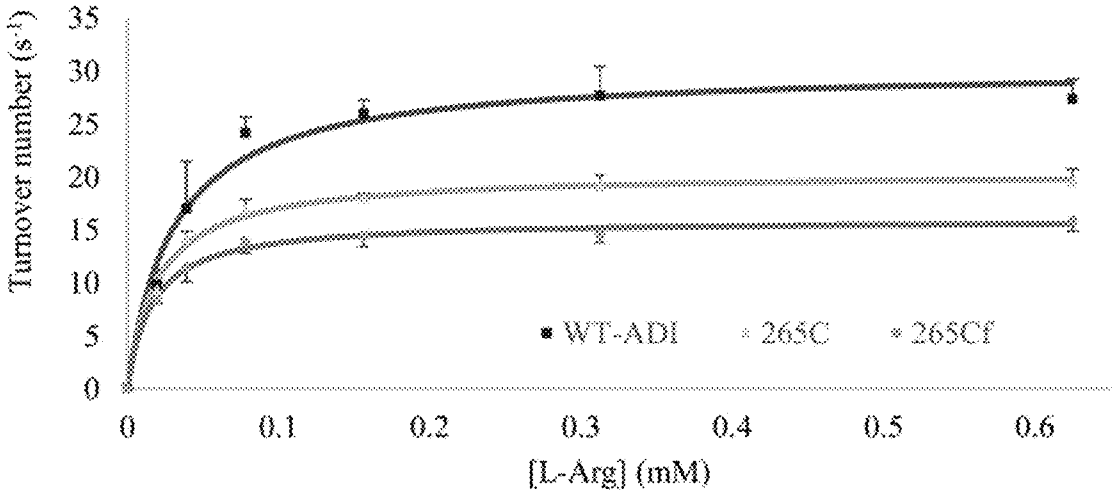
FIG. 4 depicts the kinetic profiles of wild-type arginine deiminase (WT-ADI), 265C and 265Cf. The results were expressed as means±S.D.
Figure 11:
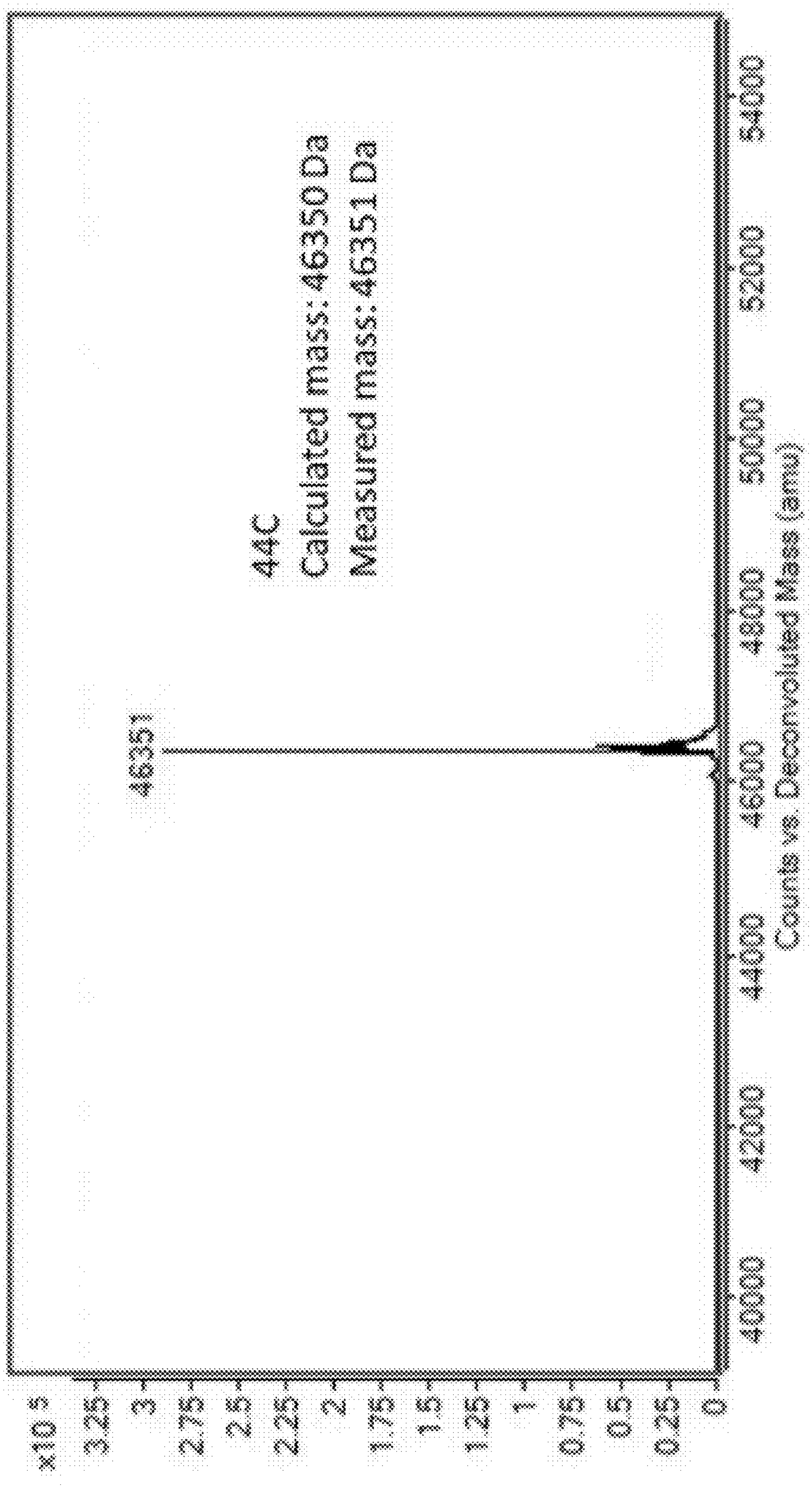
FIG. 11 depicts ESI-MS spectra of (A) 44C and (B) 44Cf.
Figure 11:
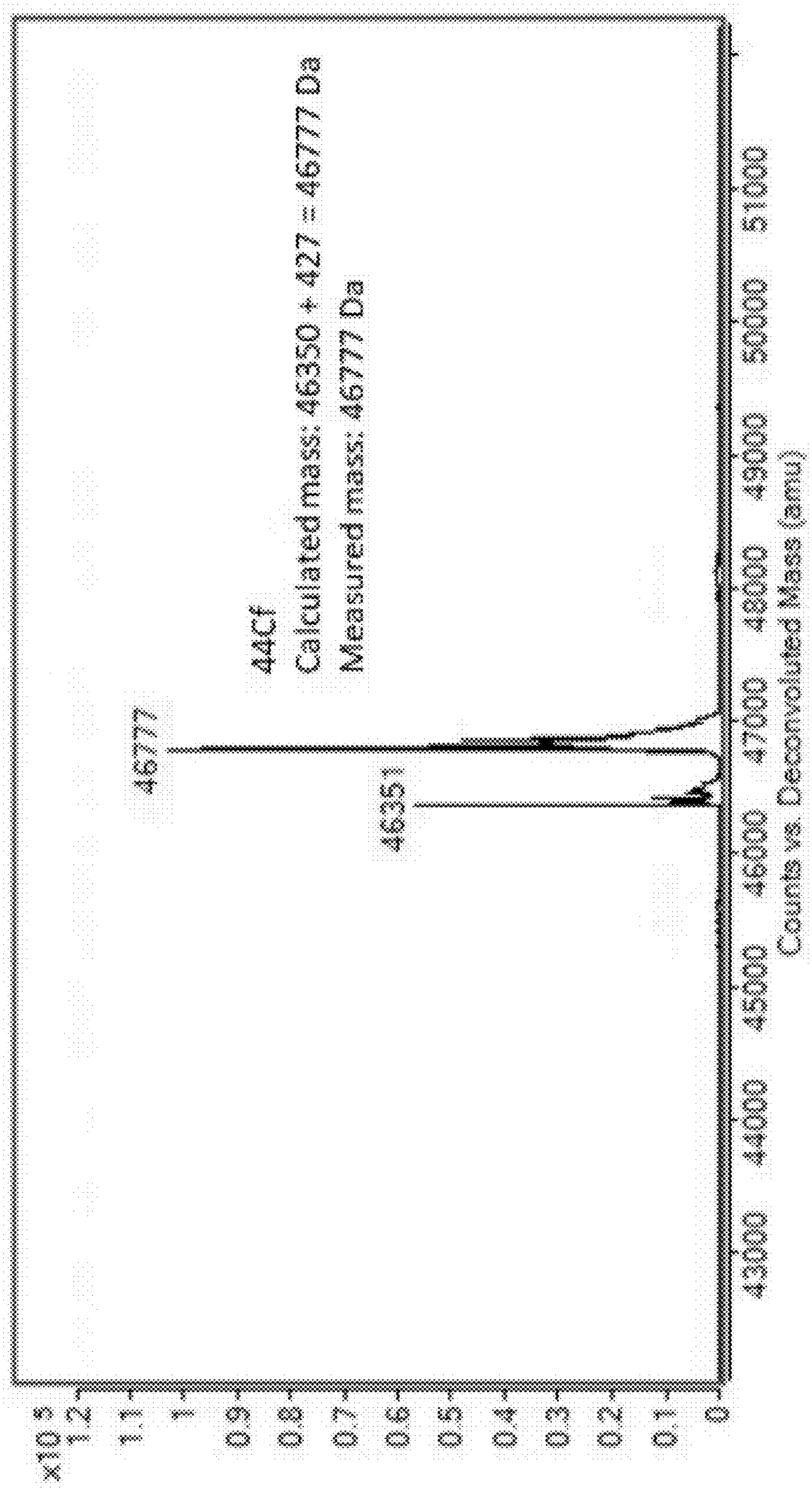
Figure 12:
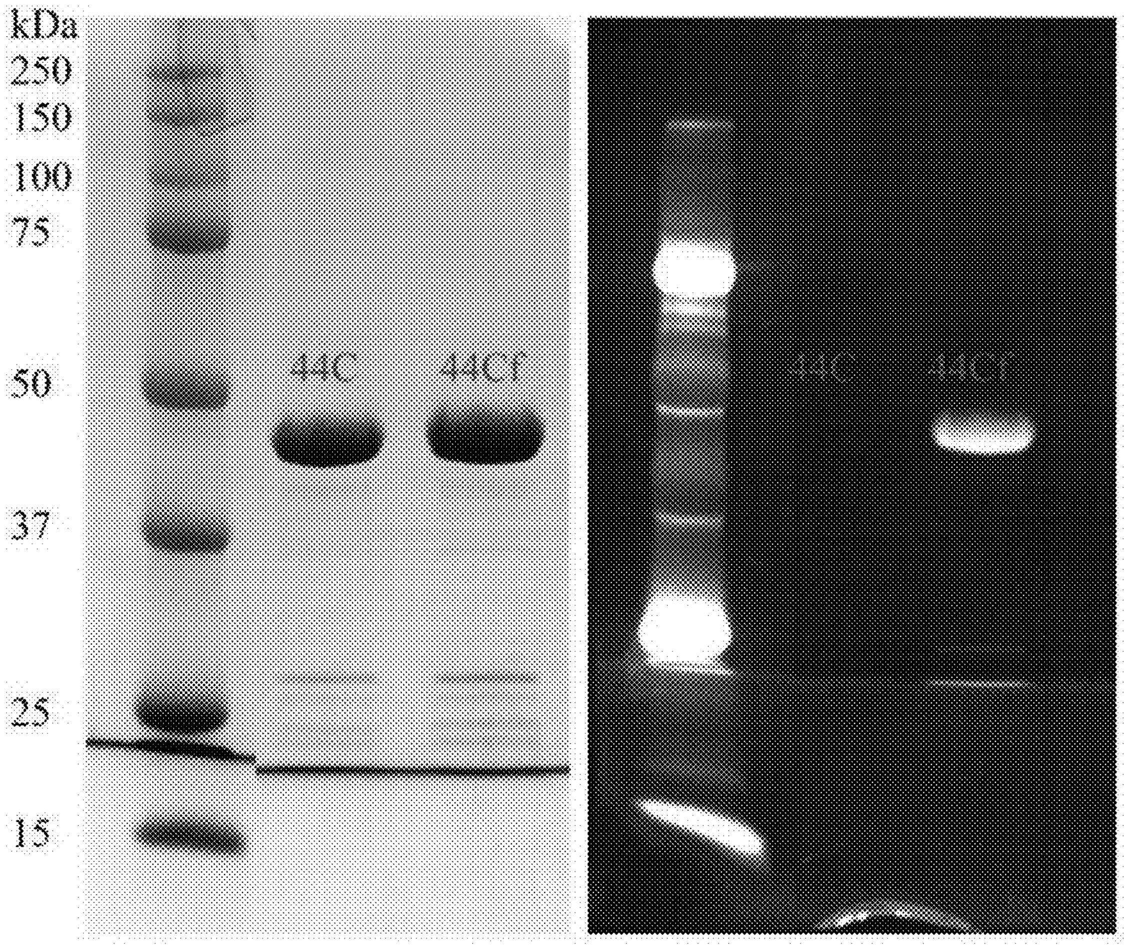
FIG. 12 depicts SDS-PAGE analysis of 44C before and after labelled with fluorescin-5-malemide. (A) Staining with Coomassie Blue. (B) Exposure under ultraviolet light.
Figure 15:
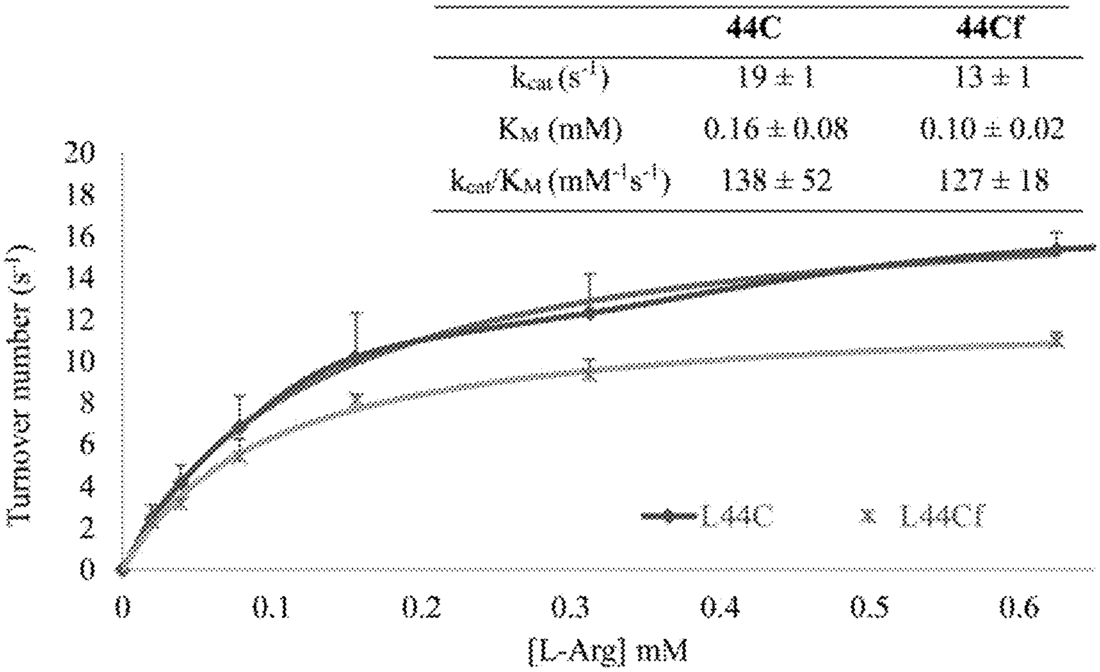
FIG. 15 depicts the kinetic profiles of L44C and L44Cf. The results were expressed as means±S.D.

We rationally selected two sites, which were $Leu^{44}$ on a beta-sheet and $Thr^{265}$ on a flexible loop, to be mutated as cysteine residue on ADI. They were located at the entrance of the solvent channel, where took part in the structural conformation changes upon substrate binding. To avoid unspecific labelling, the intrinsic $Cys^{251}$ present on ADI was mutated into $Ser^{251}$, namely C251S. Using C251S as a template, mutations on $Leu^{44} \rightarrow Cys^{4}$ and $Thr^{265} \rightarrow Cys^{265}$ were introduced to generate two mutants (44C and 265C) and these two mutants were individually site-specific labelled by F5M to become 44Cf and 265Cf. It was interesting to note that 44Cf had a 7-fold decrease in the catalytic efficiency than the wild-type (WT-ADI) whilst 265Cf showed a conserved catalytic efficiency (FIGS. 4 and 15). On the other hand, complete labelling succeeded in 265Cf, but not in 44Cf (FIGS. 1C and 11B). Based on these results, 265Cf was chosen as a candidate for the detection of L-Arg concentration.

Figure 5:
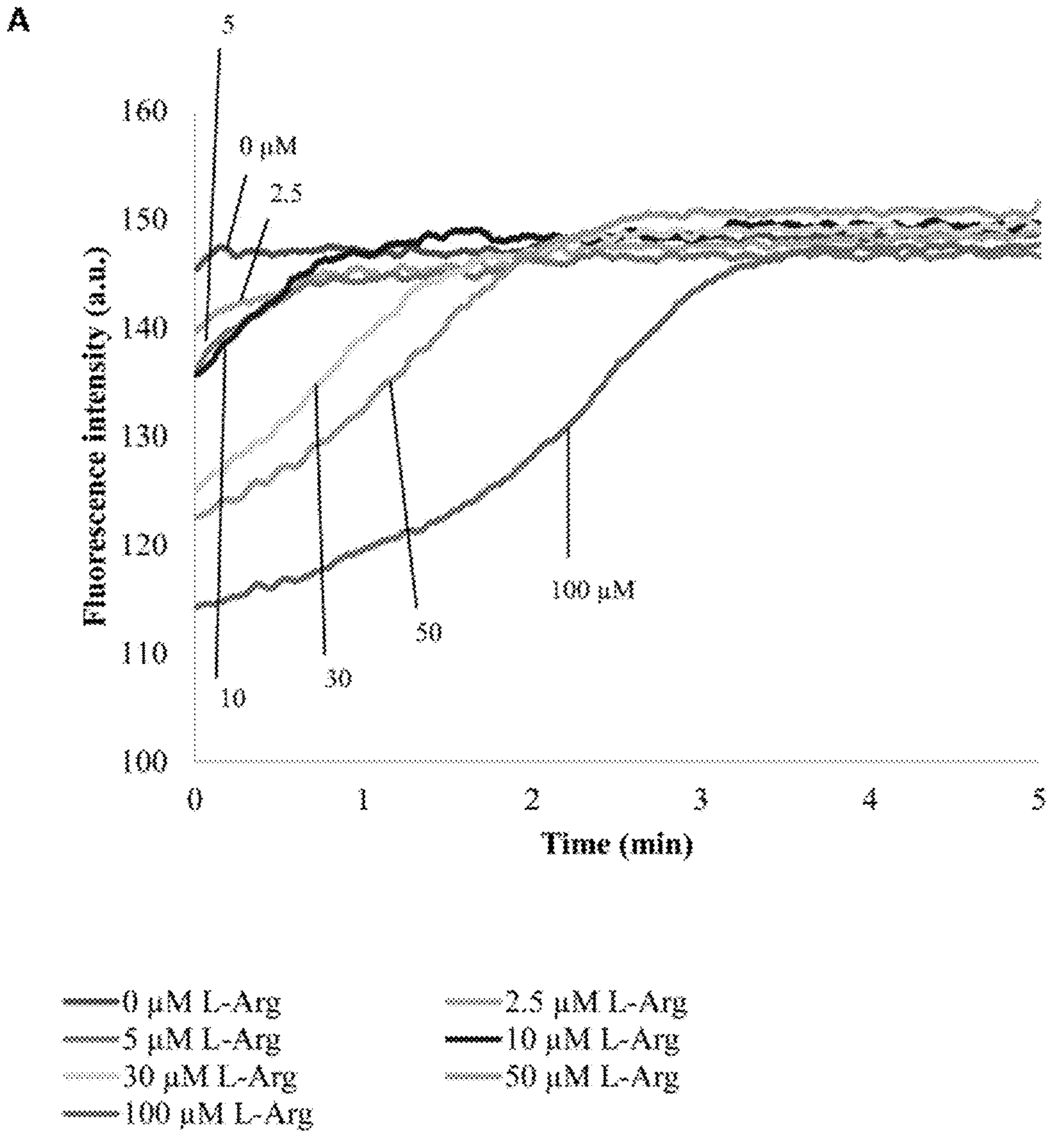
FIG. 5 depicts time-course fluorescence measurements on two fluorescein-labelled mutants (44Cf and 265Cf) with different concentrations of L-Arg in PBS solution. L-Arg in different concentrations (0-100 μM) was mixed with (A) 44Cf and (B) 265Cf, respectively. The relationship between the percentage changes of fluorescence intensities and L-Arg concentrations in 44Cf and 265Cf was shown in (C) and (D), respectively.
Figure 5:
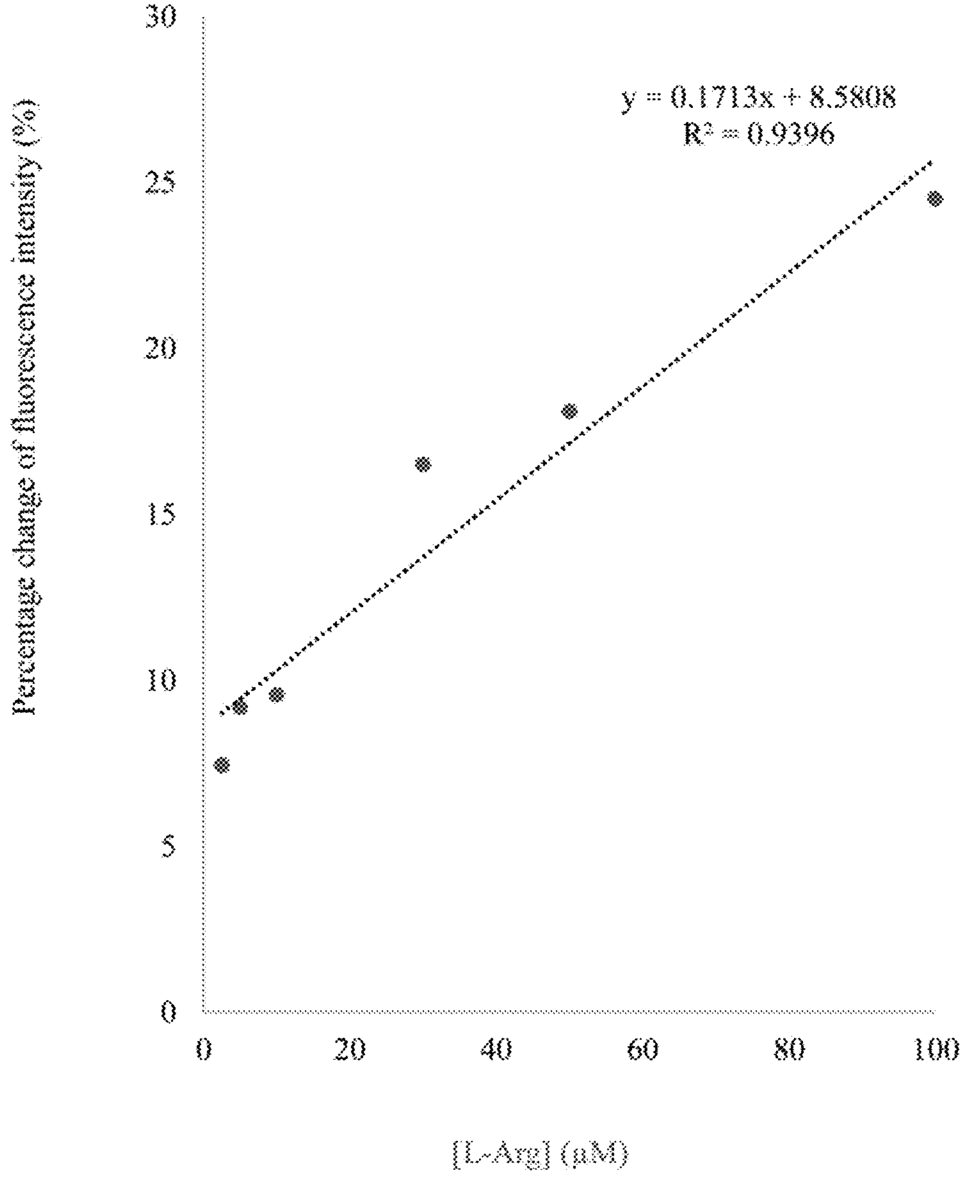
Figure 5:
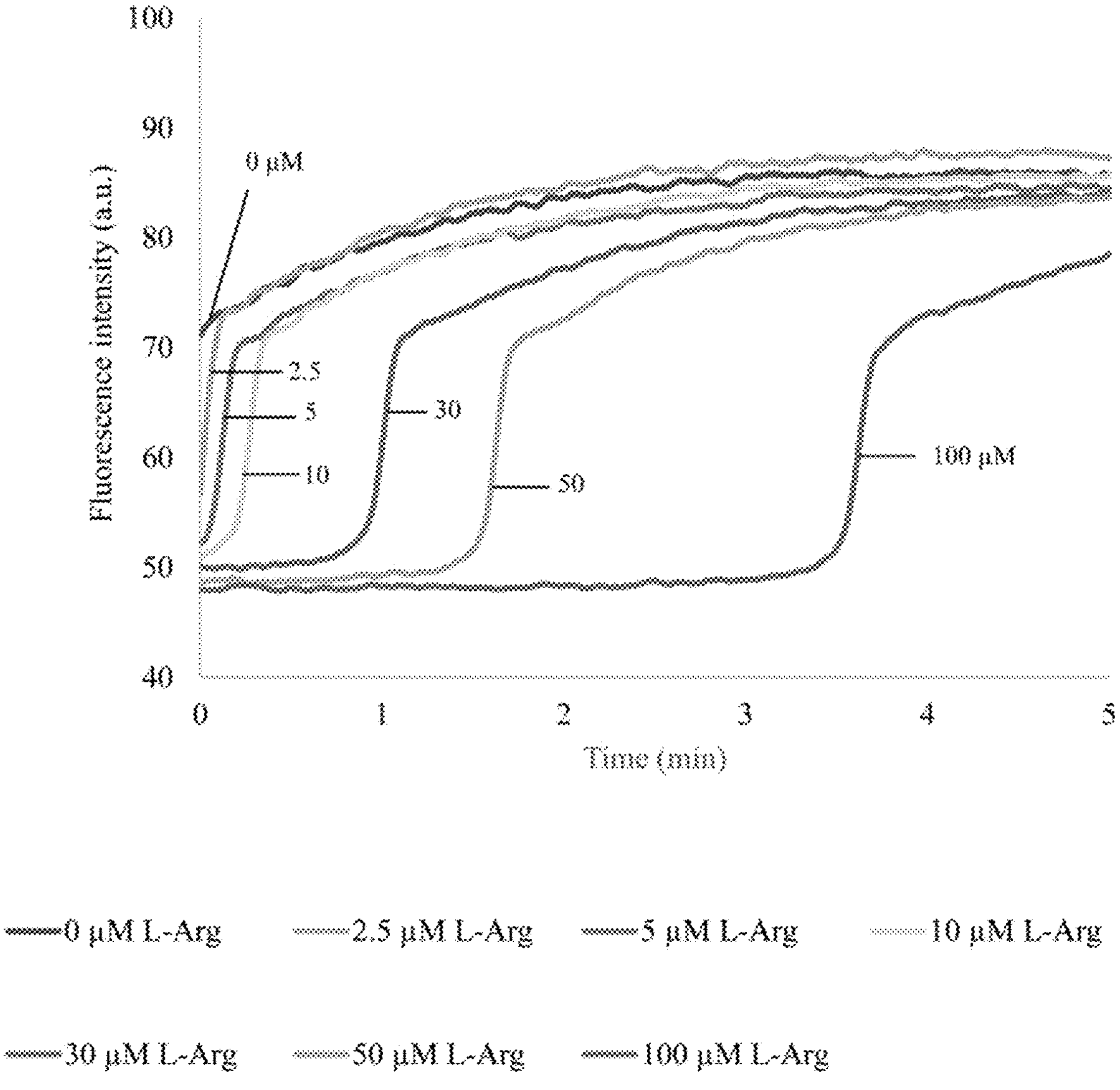
Figure 5:
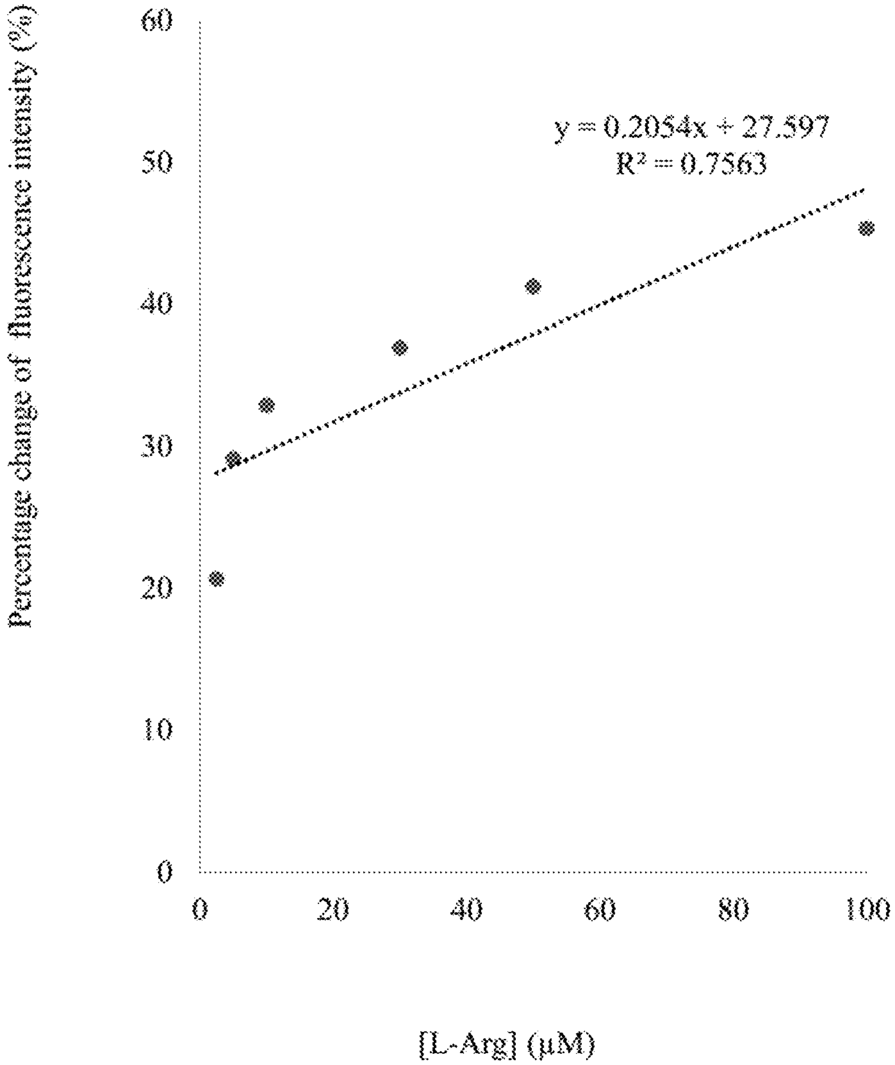

Conventional fluorescent biosensors make use of the relationship between the percentage fluorescence changes and the concentrations of analytes. However, this relationship was only found in 44Cf, but not in 265Cf. It was observed that the fluorescence intensity increased slightly with respect to the increase in L-Arg concentration in 44Cf (FIG. 5A). In contrast to 44Cf, the fluorescence changes generated by 265Cf remained almost the same when the concentration of L-Arg increased (FIG. 5C). Neither of them showed a good linear relationship between percentage fluorescence changes and L-Arg concentrations (FIGS. 5B and 5D).

Figure 6:
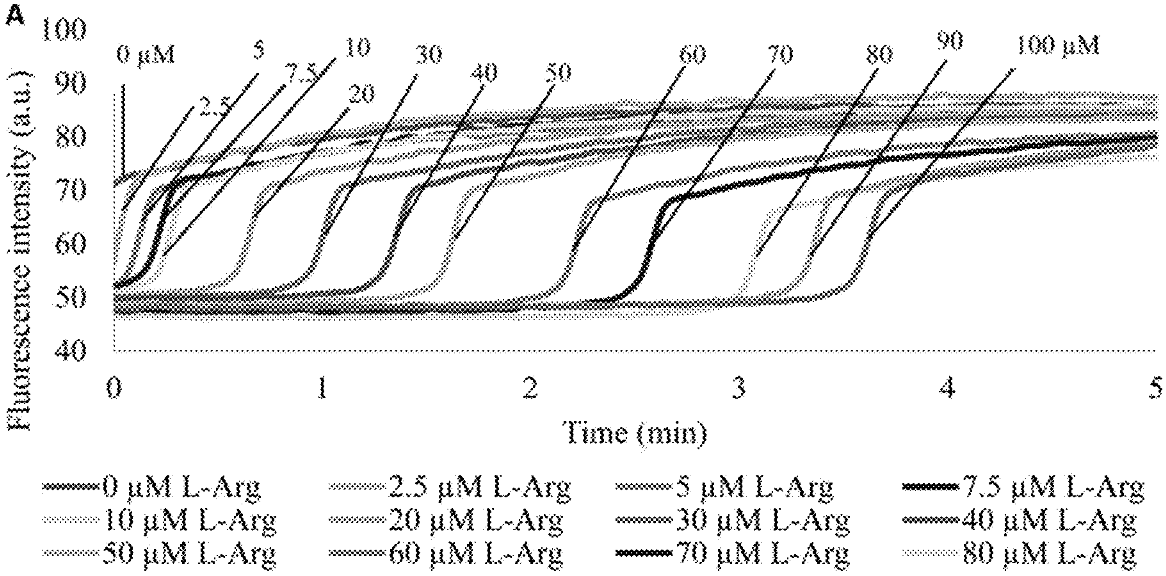
FIG. 6 depicts time-course fluorescence measurements on 265Cf in different concentrations of L-Arg in PBS solution. L-Arg in different concentrations (0-100 μM) was mixed with (A) 265Cf. (B) The rates of the fluorescence changes at different concentrations of L-Arg. (C) The linear relationship between the time at the maximum rate of the fluorescence change and the L-Arg concentration.
Figure 6:
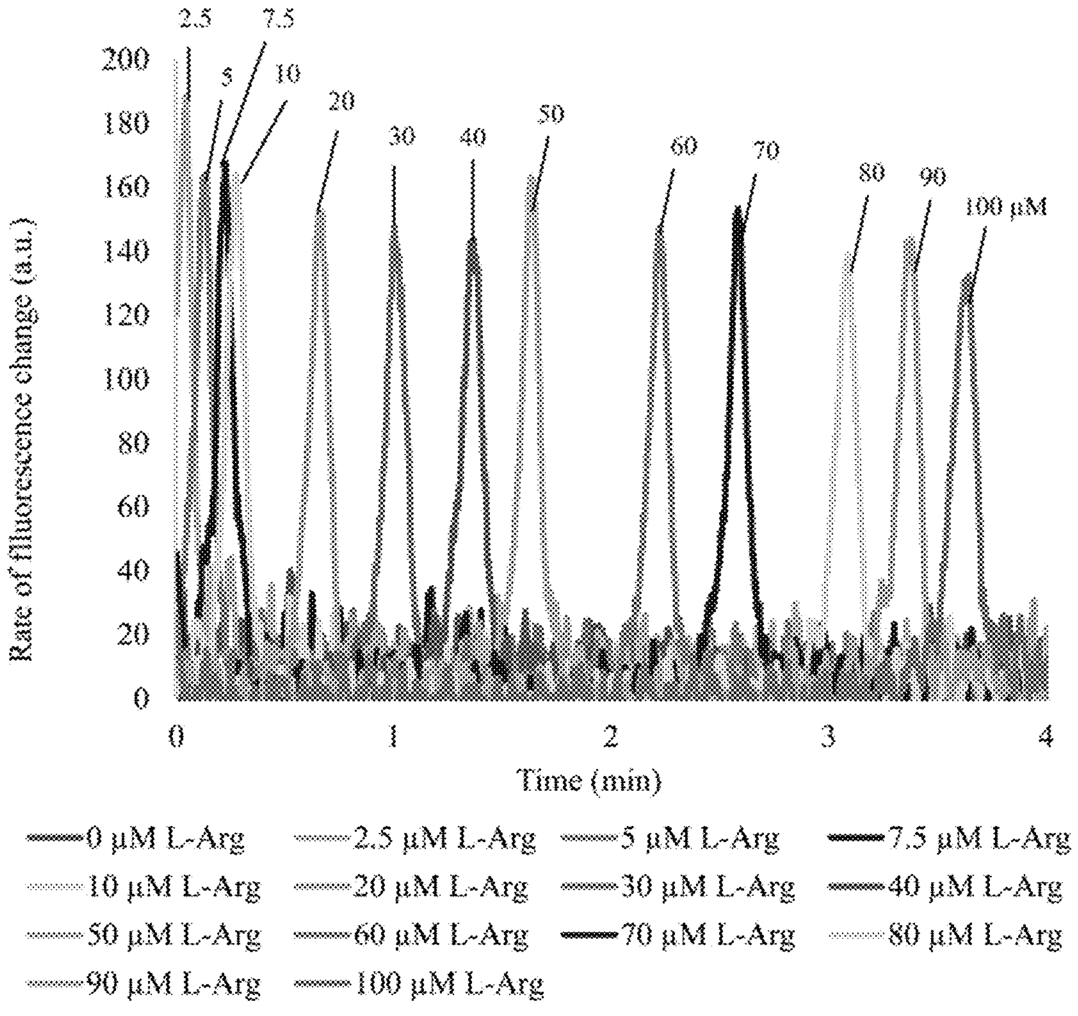
Figure 6:
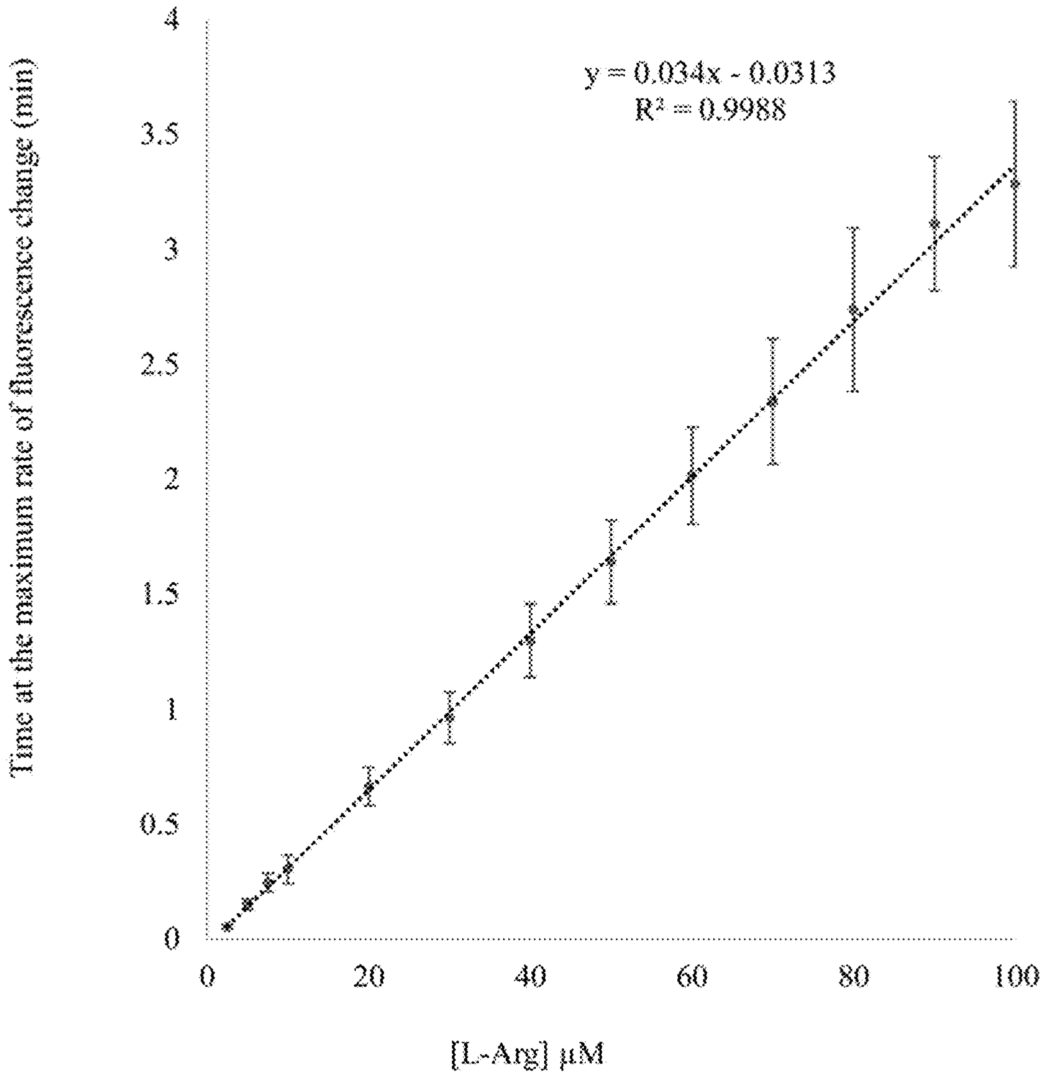
Figure 7:
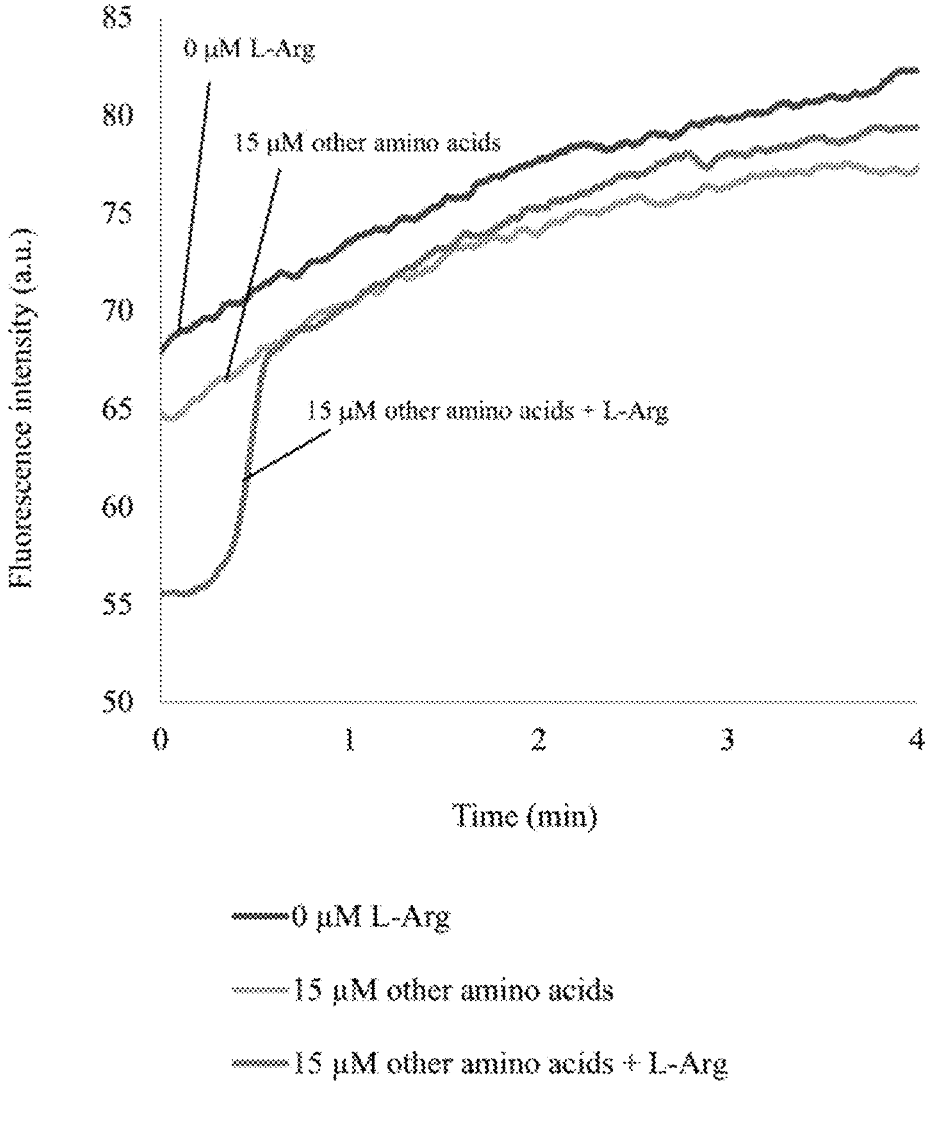
FIG. 7 depicts time-course fluorescence measurements on 265Cf mixed with 15 μM amino acid solution with and without the presence of L-Arg. (A) 15 μM amino acid solution, including asparagine, aspartic acid, agmatine, citrulline, glutamine and glutamic acid, with and without the presence of L-Arg (B) The rates of the fluorescence changes of 265Cf mixed with 15 μM amino acid solutions with and without the presence of L-Arg.
Figure 7:
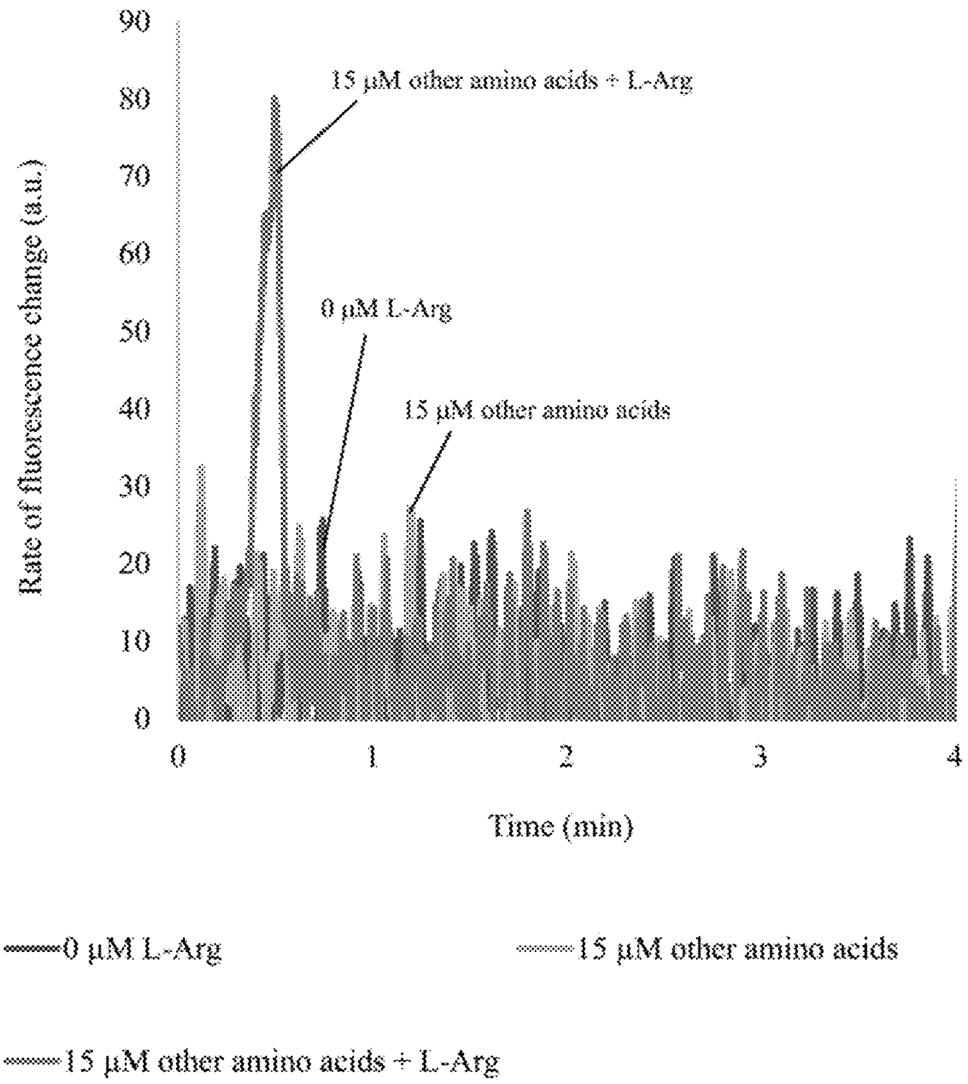
Figure 9:
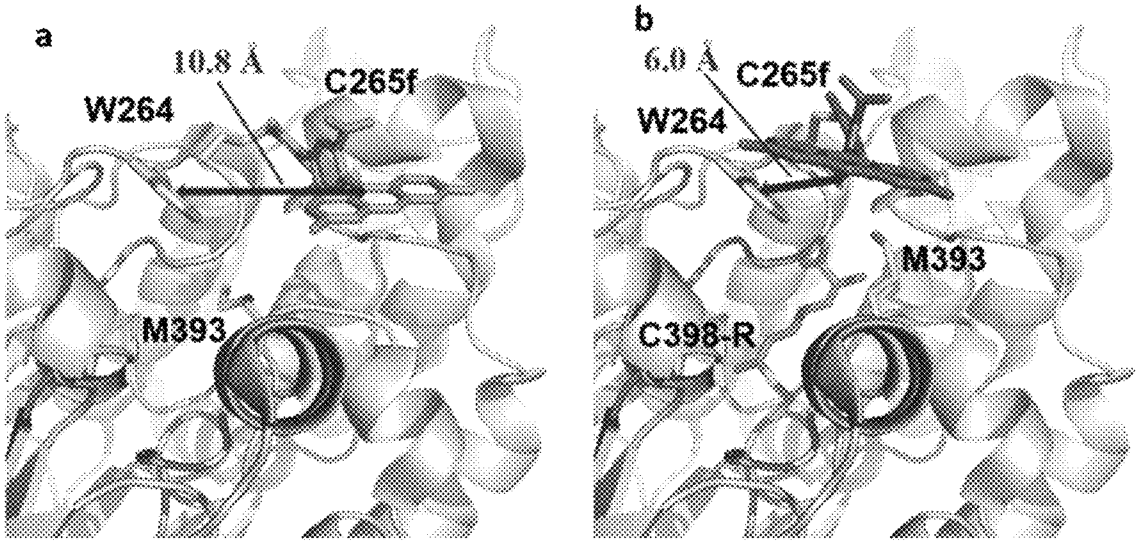
FIG. 9 depicts molecular models of arginine deiminase in the absence and presence of L-Arg. (A) In the apo-protein, the fluorescein moiety (light green) was remote from $Trp^{264}$ while $Met^{393}$ occupied part of the empty active site. The distance between the $Trp^{264}$ side chain and the fluorescein moiety was measured as 10.8 Å. (B) When L-Arg bound to $Cys^{398}$, $Met^{393}$ was pushed outward and caused the fluorescein moiety to be when it moved closer to $Trp^{264}$. The distance between the $Trp^{264}$ side chain and the fluorescein moiety was measured as 6.0 Å.

However, in 265Cf, it was discovered that the duration of fluorescence quenching was prolonged when the concentration of L-Arg increased in phosphate-buffered saline (PBS) system (FIG. 6A). This quenching was only observed in the presence of L-Arg, but not other amino acids, showing a high specificity of the fluorescent biosensor (FIG. 7). It was postulated that residue $Trp^{2}$ contributed to quenching the fluorescence of the fluorescein moiety. Results from the modelling study illustrated that $Trp^{264}$ could act as a quencher when the fluorescein moiety moved closer towards it as a result of L-Arg occupying the active site of 265Cf (FIG. 9). With this feature, 265Cf showed a correlation between the time at its maximum rate of fluorescence change and L-Arg concentration (FIG. 6B). They were linearly proportional to each other with $R^2$=0.9988 (FIG. 6C). The detection range was 2.5 to 100 μM and the assay time was 0.15-4 minutes, providing rapid quantitative measurement of L-Arg levels. The fluorescent biosensor could achieve a higher sensitivity (2.5 μM) than the existing L-Arg biosensors (Table 1).

TABLE 1

Different types of L-Arg biosensors

| Analyte | Bio-receptor | Transducers | Working systems | Immobilization | Detection range (μM) | Response time (s) |
|---|---|---|---|---|---|---|
| $NH_3$ | Arg/Urs | Conducto metric | Au coated ceramic plate | Cross-linking | 100-1000 | — |
| $NH_3$ | Arg/Urs | Conducto metric | Two Au-interdigitated film electrodes | Cross-linking | 10-4000 | 120 |
| $NH_3$ | Arg/Urs | Potentio metric | Glass electrode | Cross-linking | 25-310 | 600 |
| $NH_3$ | Arg/Urs | Ampero metric | Three-electrode system | Electro-polymerization | 70-600 | 10 |
| $NH_3$ | Arg/Urs | Fluorescent | O17-Ec membrane | Entrapment | 100-10000 | ~290 |
| $NH_3$ | Arg/Urs | Conducto metric | Fused $Al_2O_3$ with Au interdigitated electrodes | Entrapment | 2.5-500 | 20 |
| $NH_3$ | Arg/Urs | Ampero metric | Three-electrode system | Electro-polymerization | 150-600 | 60 |

TABLE 1-continued

Different types of L-Arg biosensors

| Analyte | Bio-receptor | Transducers | Working systems | Immobilization | Detection range (μM) | Response time (s) |
|---|---|---|---|---|---|---|
| $NH_3$ | ADI | Ampero metric | PANi composite screed-printed electrode | Cross linking | 3-200 | 15 |
| $NH_3$ | ADI | Potentio metric | Nanocomposite file modified glassy carbon electrode | Cross linking | 100-1000 | 10 |

Figure 8:
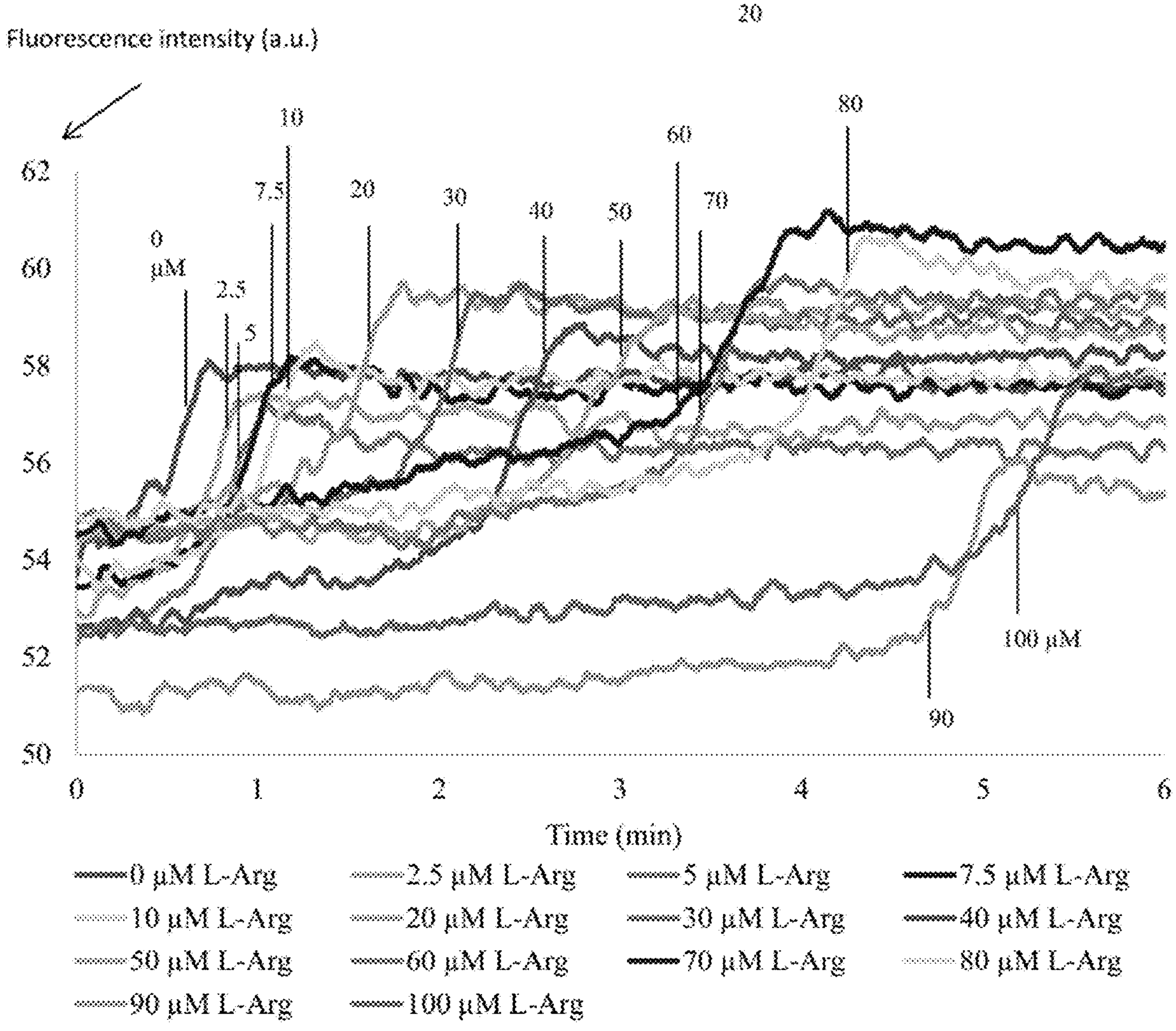
FIG. 8 depicts time-course fluorescence measurements on 265Cf (Batch 1) in different concentrations of L-Arg in fetal bovine serum. L-Arg in different concentrations (0-100 μM) was spiked into serum and mixed with (A) 265Cf. (B) The rates of the fluorescence changes at different concentrations of L-Arg. (C) The linear relationship between the time at the maximum rate of fluorescence change and the L-Arg concentration.
Figure 8:
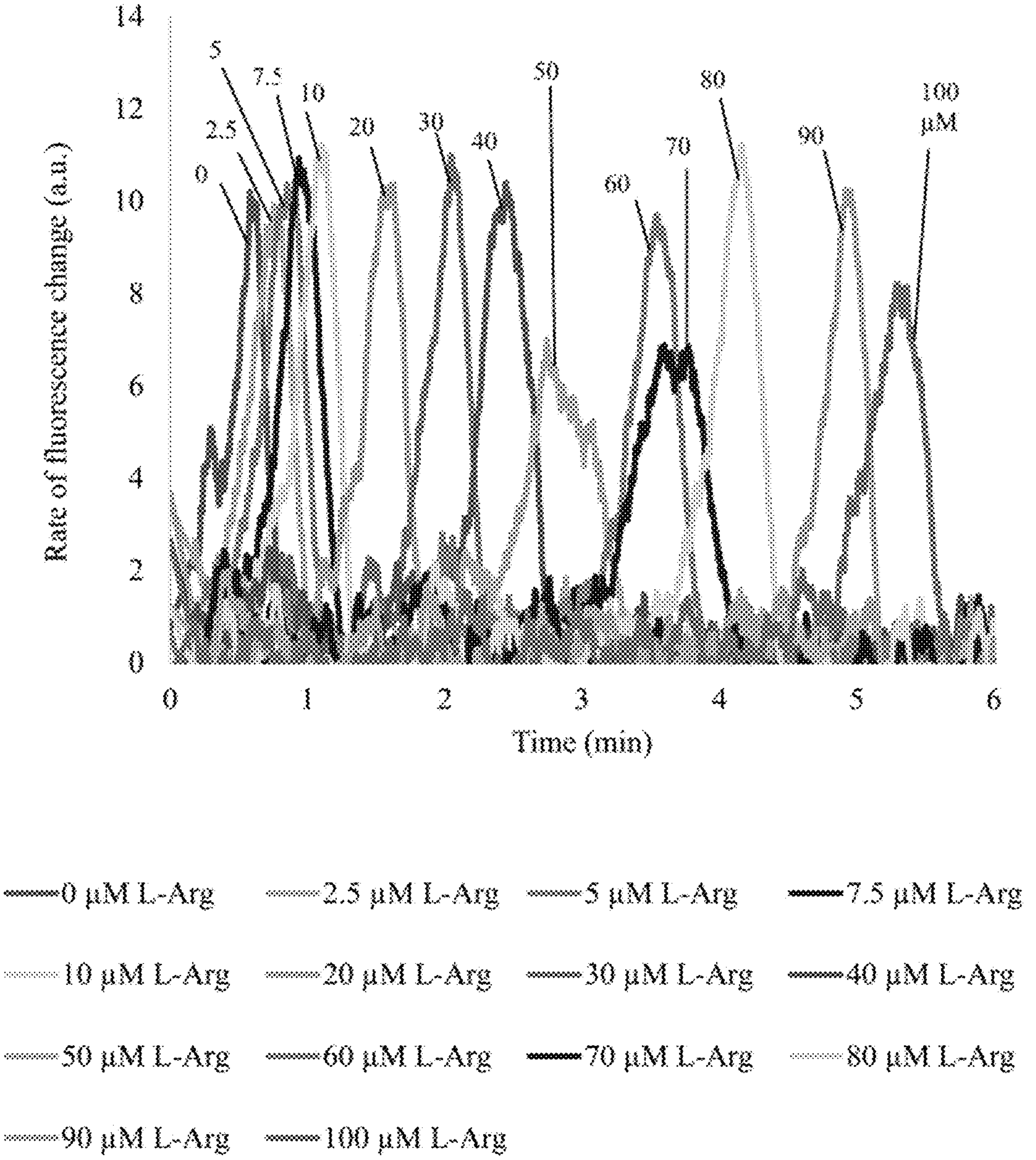
Figure 8:
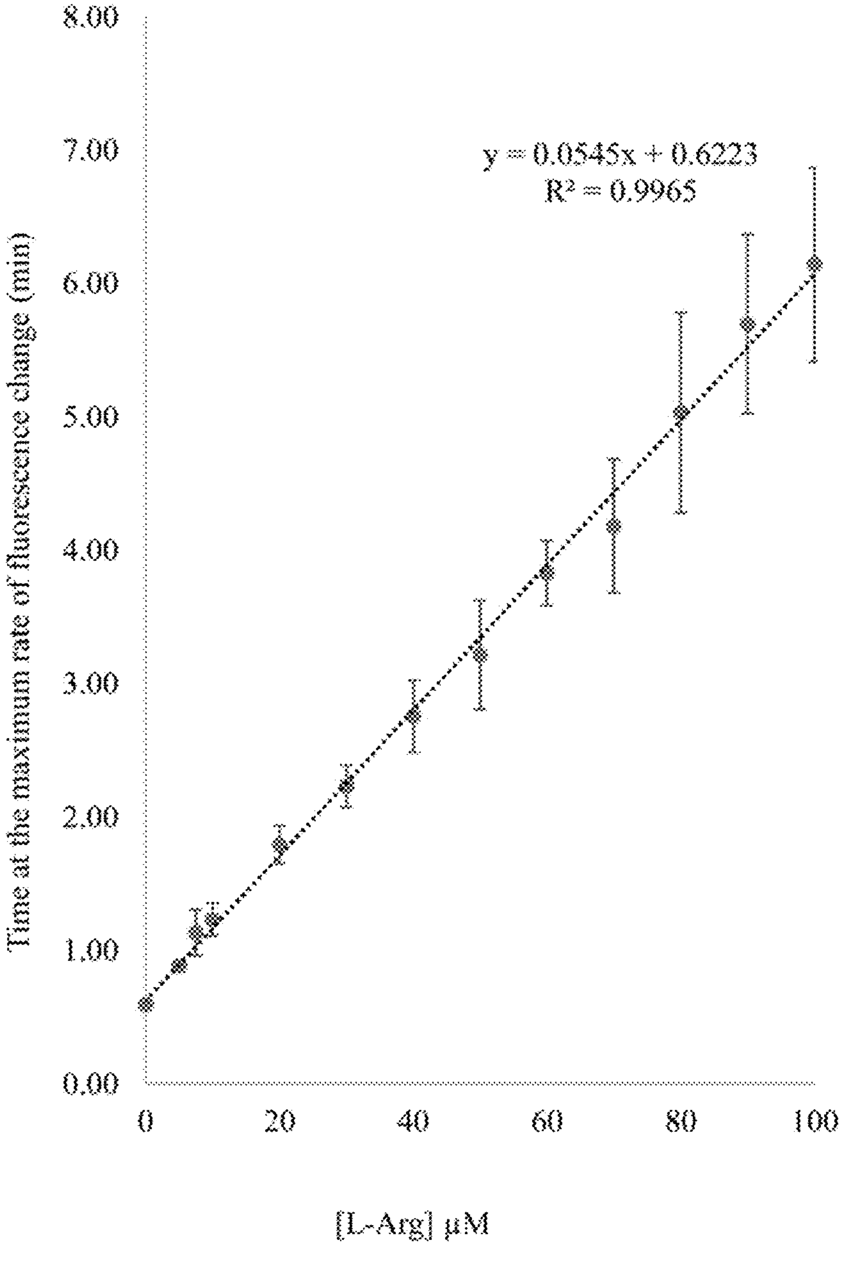
Figure 17:
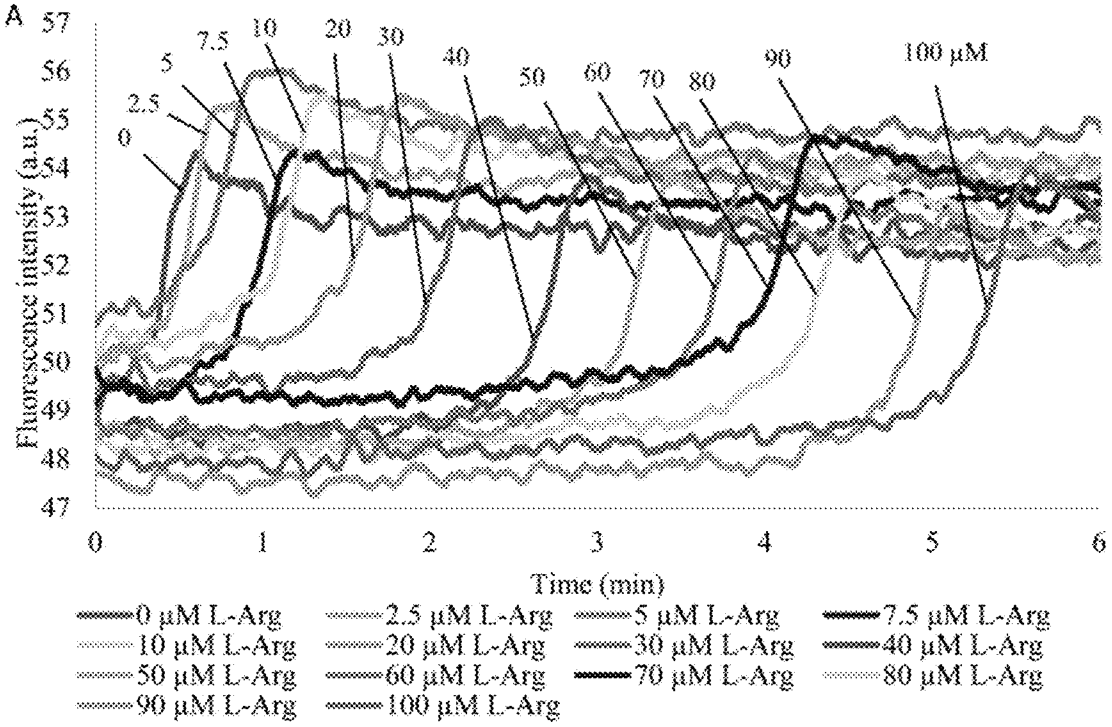
FIG. 17 depicts time-course fluorescence measurements on 265Cf (Batch 2) in different concentrations of L-Arg in fetal bovine serum. L-Arg in different concentrations (0-100 μM) was spiked into serum and mixed with (A) 265Cf. (B) The rates of the fluorescence changes at different concentrations of L-Arg. (C) The linear relationship between the time at the maximum rate of fluorescence change and the L-Arg concentration.
Figure 17:
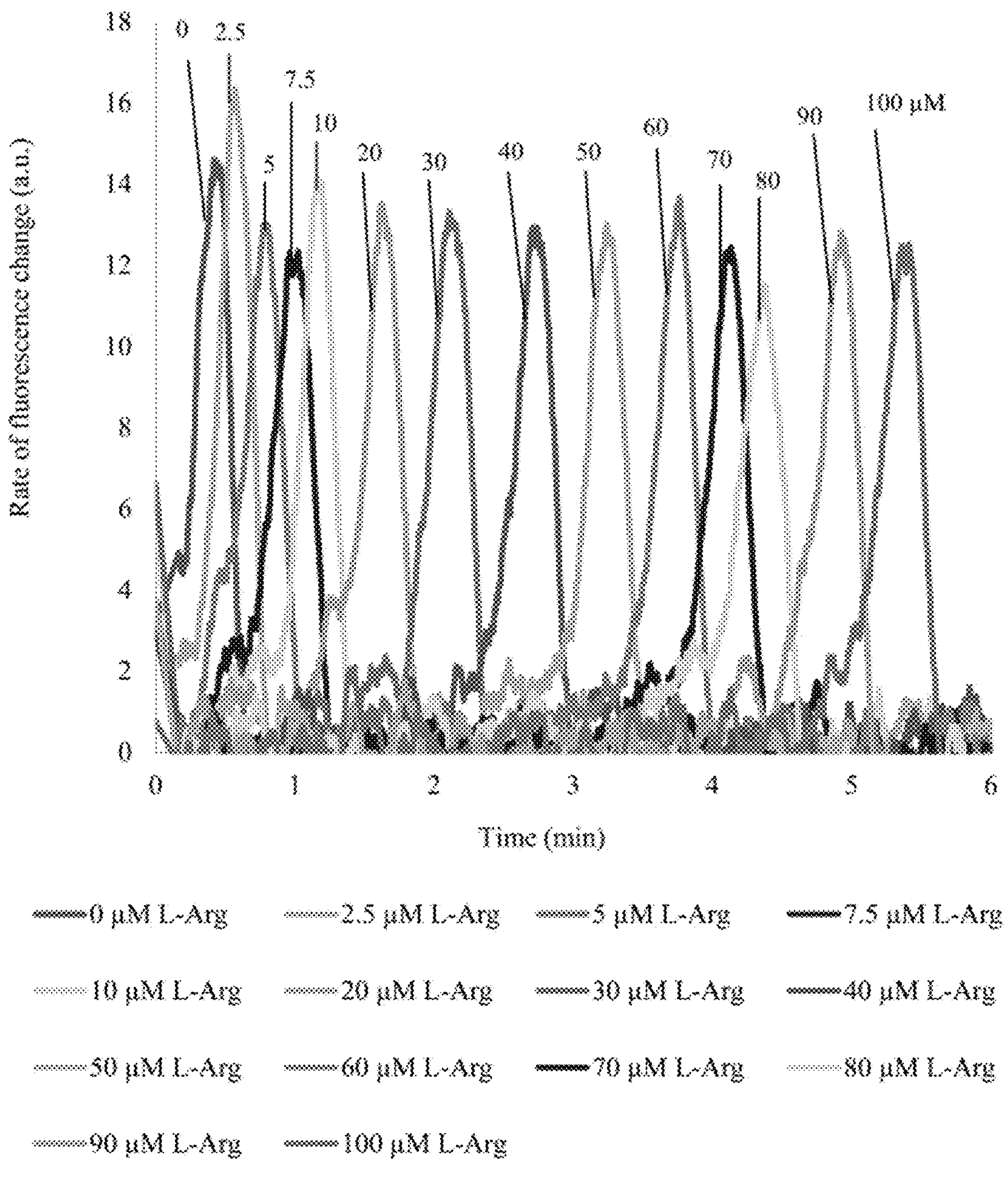
Figure 17:
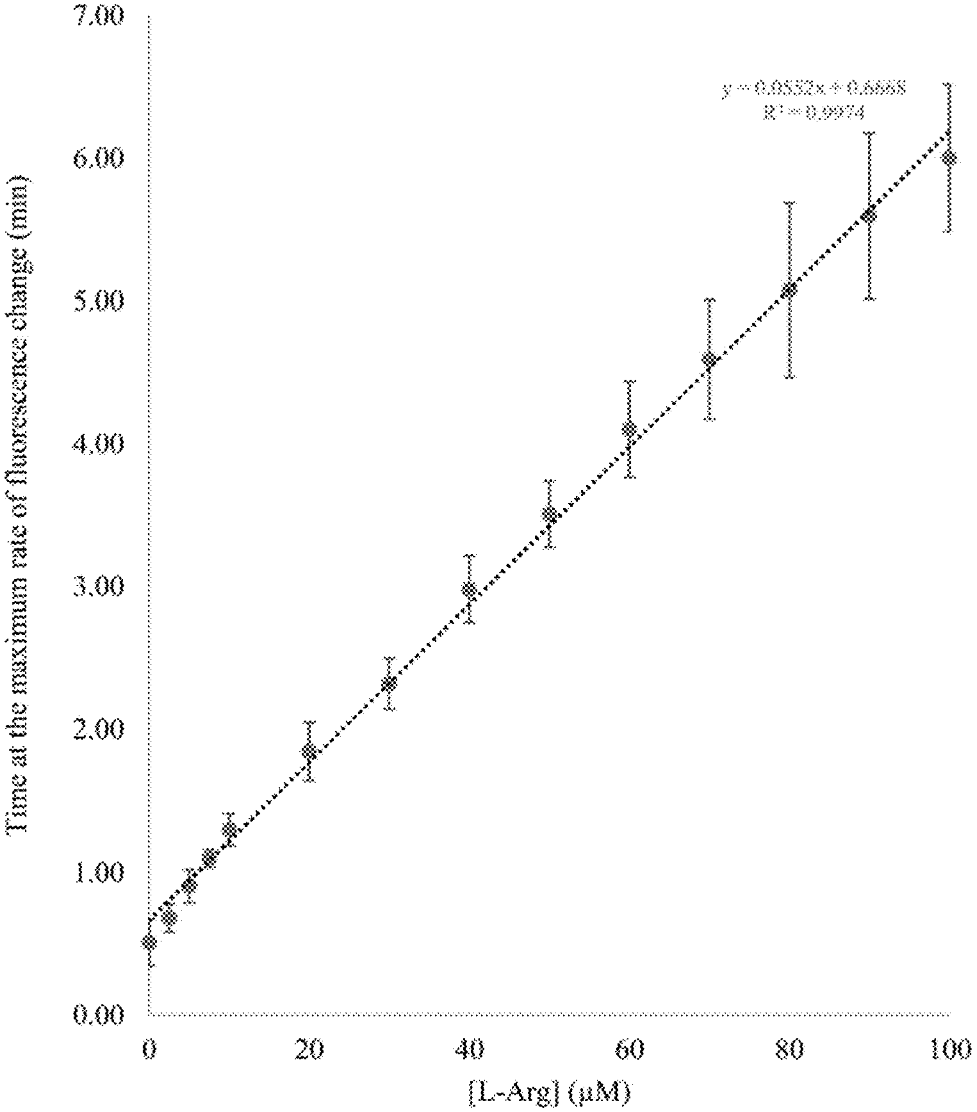

Notes:
Arg: Arginases;
Urs: Ureases;
ADI: arginine deiminase;
O17-Ec: oxazine 170 perchlorate-ethyl cellulose;
PANi: Polyanyline With a high sensitivity and specificity, the fluorescent biosensor, 265Cf, was used in connection with biological samples (more complicated matrix systems) for the determination of L-Arg. It demonstrated a quantitative analysis of fetal bovine serum without the need of sample pre-treatment. The pattern of the resulting fluorescence changes was similar to the one measured in the PBS system, but the fluorescence intensity changes significantly reduced and the times at the maximum rate of fluorescence change shifted due to the matrix interferences (FIGS. 8A and 8B). By using a standard addition method, the L-Arg concentration in serum determined by two different batches of biosensor were 47.2±6.0 μM and 48.9±1.2 μM L-Arg, which were in good agreement with the results obtained from mass spectrometry (48.3±1.5 μM) (FIGS. 8C, 17C and Table 3). This showed the potential use of 265Cf on matrix-complicated systems, such as biological samples. Furthermore, the fluorescent biosensor exhibited good linearity at low concentration range of L-Arg in the standard addition method, suggesting it could be a rapid clinical tool for the measurement of low L-Arg concentration in samples, such as human serum from cancer patients treated with arginine-depleting drugs or enzymes.

A fluorescent biosensor (265Cf) was developed by site-specific attachment of fluorescein-5-maldeimide (F5M) to generate fluorescence quenching, which was induced by the structural conformational changes of the bioengineered ADI as a result of L-Arg binding. A linear relationship between the time at the maximum rate of the fluorescence change and the concentrations of L-Arg was revealed. The linear detection range was 2.5-100 μM with good linearity of $R^1$=0.9988. The assay response time was 0.15-4 min, which was comparable to that of the existing L-Arg biosensors. By using the standard addition method, 265Cf could be applied to the detection of L-Arg in animal serum (e.g. bovine serum) without any sample pre-treatment, showing its potential use on clinical, food and pharmaceutical samples. Our study demonstrated a simple strategy for making a biosensor to provide an alternative method for the rapid determination of L-Arg concentration. This strategy is universal and provides insight on the detection of biological samples by using site-specific fluorophore-labelled enzymes.

EXAMPLES

Materials and Methods

The DNA sequence of wild-type arginine deiminase (WT-ADI) inserted into pET3a vector, pET3a/WT-ADI, was purchased from GeneScript. Fluorescein-5-maleimide (F5M) was purchased from Invitrogen. L-Arg and fetal bovine serum (HyClone™) were purchased from ThermoFisher. Fluorescence measurements were performed on an Agilent Cary Eclipse Fluorescence Spectrophotometer (Agilent). Electrospray ionization mass spectrometry (ESI-MS) experiments were conducted using an Agilent 6540 QTOF mass spectrometer coupled with an Agilent 1290 Infinity UHPLC system.

Gene Cloning and Mutagenesis

Plasmid pET3a/WT-ADI was used as a template for site-directed mutagenesis according to the instruction of the QuikChange site-directed mutagenesis kit (Strategene). The codon for $Cys^{251}$ residue was mutated to the codon for $Ser^{251}$ using the following mutagenic primers. The mutated ADI was named as C251S.

Forward primer of C251S: 5' GTTGCTAATAAAGAAAGCGAATTC AAACGTATT 3' (SEQ ID NO: 5)

Reverse primer of C251S: 5' AATACGTTTGAATTCGCTTTCTTTATTAGCAAC 3' (SEQ ID NO: 6)

The plasmid pET3a/C251S was then used as a template for further site-directed mutagenesis to respectively generate two mutants by the following primers. They were named as 44C and 265C.

Forward Primer of 44C:

```
                                        (SEQ ID NO: 7)
5'
GACTATATTACACCAGCTAGACTAGATGAATTATGCTTCTCAGCTATC
TTAGAA 3'
```

Reverse Primer of 44C:

```
                                        (SEQ ID NO: 8)
5'TTCTAAGATAGCTGAGAAGCATTCATCTAGTCTAGCTGGTGTAATA
TAGTC 3'
```

Forward Primer of 265C:

```
                                        (SEQ ID NO: 9)
5'TGTTGCAATTAACGTTCCAAAATGGTGCAACTTAATGCACTTAGAC
ACATG GC 3'
```

Reverse Primer of 265C:

(SEQ ID NO: 10)

```
5'GCCATGTGTCTAAGTGCATTAAGTTGCACCATTTTGGAACGTTAAT
TGCA ACA 3'
```

Expression and Purification of ADI

Plasmids corresponding to WT-ADI and two mutants (44C and 265C) were transformed into BL21(DE3) for expression. A single colony was picked and grown overnight at 37° C. in sterile LB medium that contained 100 μg/ml ampicillin with shaking at 250 rev/min. The overnight culture was inoculated into 600 mL sterile LB medium with 100 μg/ml ampicillin in a ratio of 1:100 and grown at 37° C. with shaking at 250 rev/min for 2-3 hours. When the culture optical density ($OD_{600}$) reached 0.6-0.8, one millimolar of IPTG was added for protein expression. The cell pellet was collected by centrifugation and lysed by an ultrasonic homogenizer (QSonica sonicators) in resuspension buffer (20 mM Tris buffer, pH 7.0). The crude cell lysates were centrifugated at 14,000 rpm for 2 h at 4° C. The insoluble form was collected by centrifugation and resuspended in resuspension buffer for sonication. After that, it was collected by centrifugation at 14,000 rpm at 4° C. and washed by washing buffer twice (20 mM Tris, 1 mM EDTA, pH 7.0, and 4% Triton X-100). The resulting inclusion bodies were solubilized in a denaturing buffer (50 mM Tris, pH 8.5, 6M guanidine-HCl, and 10 mM dithiothreitol) for 1 h at 37° C. The solubilized proteins were refolded in a 100-fold excess volume of 20 mM Tris buffer, pH 7.0 at room temperature overnight. They were then purified by HiTrap Q HP (GE Healthcare). Target proteins were eluted at 20% of elution buffer (20 mM Tris, pH 7.0, 1 M NaCl) and analysed by sodium dodecyl sulfate polyacrylamide gel electrophoresis (SDS-PAGE).

Bicinchoninic Acid (BCA) Protein Assay

Pierce™ BCA protein assay was used to determine the protein concentration following the manufacturer's instruction (Thermo Fisher Scientific).

Protein Labelling

F5M was labelled as described with the following modifications. The ADI mutants were buffer exchanged into 20 mM Tris, pH 7.0. A 10 mM stock solution of F5M was prepared by dissolving it in dimethylformamide, and added to the ADI mutants in a molar ratio of 1:20. They were incubated in the dark for 2 h with shaking. After that, excess F5M was removed by dialysis with 20 mM Tris buffer using Amicon Ultra-15 (NMWL=30,000). The ADI mutants before and after labelling were analysed by SDS-PAGE.

Enzyme Kinetics

The chromophore compound was detected at a wavelength of $A_{530\ nm}$ in the presence of diacetyl monoxime, thiosemicarbazide, urea, and $Fe^{3+}$ ions under 100° C. The amount of L-citrulline produced by arginine deiminase per second was determined. Different concentrations of L-Arg solutions (200 μL) were pre-warmed at a 37° C. heat block. Reactions were performed by adding 5 μL of ADI (0.02 mg/mL) to specified concentration of L-Arg and terminated with 15 μL 80% trichloroacetic acid. The reaction time was 3 minutes. A colouring reagent was prepared by 1 volume of a mixture of solution A (80 mM diacetyl monoxime and 2.0 mM thiosemicarbazide) and 3 volumes of a mixture of solution B (3 M $H_3PO_4$, 6 M $H_2SO_4$, 2 mM $FeCl_3$). Eight hundred microliters of the colouring reagent were added to each reaction, and then the reaction mixtures were incubated at 100° C. for 10 min in the heat block. $A_{530\ nm}$ was determined using ultraviolet-visible spectroscopy (Spectronic 20 Genesys Spectrometer).

Specific Enzyme Activity

The experimental procedure was the same as that of enzyme kinetics by using 20 mM L-Arg for the measurement. The specific activity of arginine deiminase enzyme was defined as the micromoles of L-citrulline formed per minute under given conditions per milligram proteins at 37° C., pH 7.4 in phosphate buffered saline buffer (expressed in mol $min^{-1}mg^{-1}$).

Mass Spectrometry Analysis

Liquid Chromatography-Electrospray Ionization Mass Spectrometry (LC-ESI-MS) experiments were performed with an Agilent 6540 QTOF mass spectrometer coupled with an Agilent 1290 Infinity UHPLC system. For the detection of intact proteins, samples were first injected into a C4 LC column and eluted with a linear gradient from 95% solvent A: 5% solvent B to 5% solvent A: 95% solvent B, where solvent A was 0.1% formic acid in MilliQ water and solvent B was acetonitrile with 0.1% formic acid. ESI-MS data were acquired with m/z range of 100-2500, from which multiply-charged mass spectra were obtained. The multiply charged mass spectra were deconvoluted by the MassHunter BioConfirm program (Agilent) to obtain the molecular mass of proteins. For the protein digestion experiment, proteins were first buffer exchanged into ammonium bicarbonate buffer and subsequently sequencing grade trypsin (Promega V5111) was added to the proteins in a ratio of trypsin:protein 1:50 (wt/wt). Protease digestions proceeded at 37° C. for 16 hours. Peptides were separated and eluted in a C18 LC column with a linear gradient from 95% solvent A: 5% solvent B to 5% solvent A: 95% solvent B, where solvent A was 0.1% formic acid in MilliQ water and solvent B was acetonitrile with 0.1% formic acid. The ESI-MS was operated in auto-ms/ms mode for measurement of the molecular mass of peptides and their sequence-specific fragment ions resulted from collision-induced dissociation. Peptide assignment was performed with the Agilent Masshunter-BioConfirm software.

Florescence Measurements

Different concentrations of L-Arg ranged from 2.5 to 100 μM, were prepared in PBS solution (pH 7.4). Four hundred and ninety-five microliters of each L-Arg solution was added in a quartz cuvette and mixed with 5 μL of 0.3 mg/ml of labelled ADI mutants. The real-time fluorescence intensity was recorded using an Agilent Cary Eclipse Fluorescence Spectrophotometer (Agilent). Both excitation and emission slit widths were 5 nm. The excitation wavelength was 494 nm while the emission wavelength was 518 nm.

Preparation of L-Arg Spiked in Serum and Standard Addition Assay

Fetal bovine serum (Hyclone™) was used for L-Arg detection by our biosensor. It was four-folded diluted by PBS solution. Different concentrations of L-Arg ranging from 2.5 to 100 μM, were spiked into the diluted serum. Four hundred and ninety-five microliters of each L-Arg solution spiked in serum was added in a quartz cuvette and mixed with 5 μL of 0.3 mg/ml of 265Cf. Two different batches of 265Cf were used for the determination. The real-time fluorescence intensity was recorded using a Cary Eclipse Fluorescence Spectrophotometer (Agilent). Both excitation and emission slit widths were 5 nm. The excitation wavelength was 494 nm while the emission wavelength was 518 nm.

Molecular Modelling

The substrate-bound model was created based on the crystal structure of arginine deiminase of *M. arginini* (WT-ADI) with Protein Data Bank Identifier (PDB ID) 1S9R. The fluorophore-labelled cysteine residue was built with Crystallographic Object-Oriented Toolkit (Coot) with the help of JLigand. The apo-enzyme model of WT-ADI was built based on the crystal structures of the *P. aeruginosa* homologue (Pa-ADI), of which both apo- and covalently-linked substrate complex were available (PDB IDs 1RXX and 2AAF, respectively). The substrate-bound complexes of WT-ADI and Pa-ADI were essentially superimposable, including the substrate, L-Arg. It was noticeable that in the apo-Pa-ADI structure, a side chain of residue 401 ($Arg^{401}$) occupied part of the space where the substrate bound. On substrate binding, $Arg^{401}$ gave way to the substrate and was displaced outward towards the solvent as revealed by the arginine-bound Pa-ADI. The equivalent residue of Pa-ADI $Arg^{401}$ was $Met^{393}$ in WT-ADI. These two residues were almost superimposable in both substrate-bound structures (1S9R and 2AAF). This comparison allowed modelling of the active site of apo-WT-ADI, referencing both Pa-ADI structures (1RXX and 2AAF). Residues 390-394 of apo-WT-ADI was built based on residues 398 to 402 (Pa-ADI) surrounding one side of the active site, using Coot. The figures were rendered with PyMOL. The distance between the $Trp^{264}$ side chain and the fluorescein moiety of 265Cf was defined by the midpoints between the CD2 and CE2 atoms on $Trp^{264}$ and the O2 and C10 atoms on 265f.

Protein Expression and Purification

Figure 10:
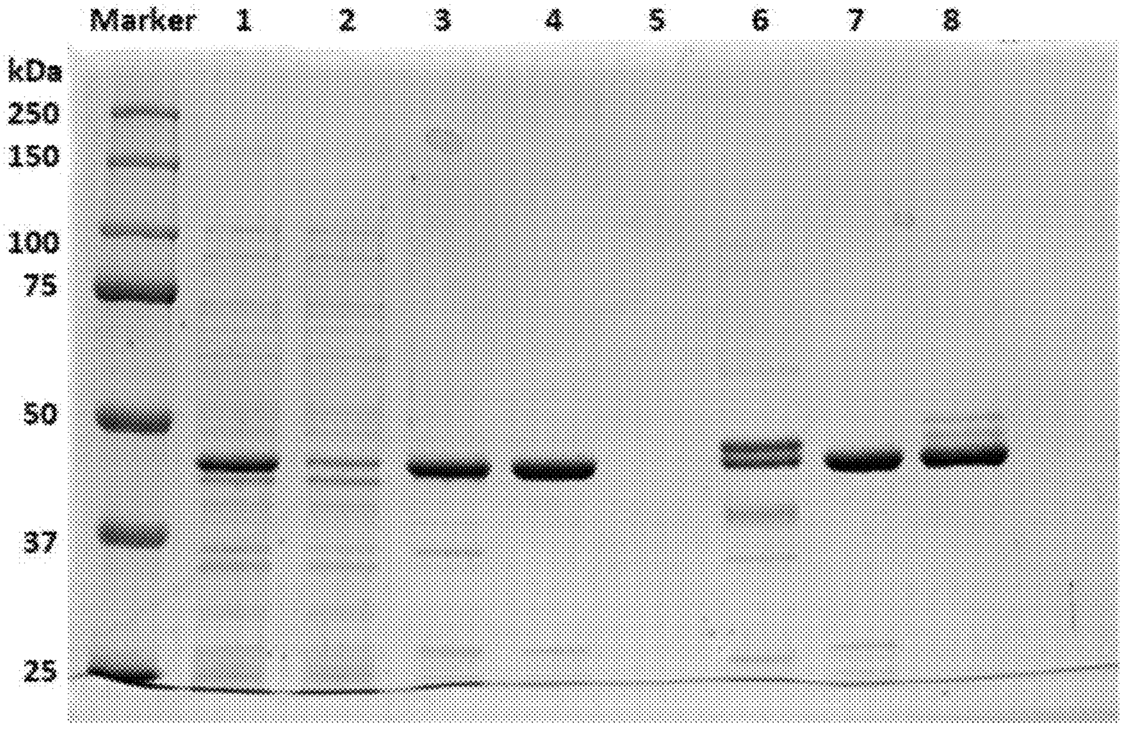
FIG. 10 depicts SDS-PAGE analysis of the expression and purification of wild type arginine deiminase (WT-ADI). Lane 1: Total lysate; Lane 2: Soluble Fraction; Lane 3: Inclusion body; Lane 4: Denatured and re-folded wild type ADI; Lane 6: Flow-through; Lane 7: 20% elution; Lane 8: 100% elution

Wild-type arginine deiminase (WT-ADI) and two corresponding mutants (44C and 265C) were expressed and purified. They were highly expressed as inclusion bodies and were purified by a single-step column with high purity (FIG. 10). High purity of WT-ADI was observed after the refolding process (FIG. 10, lane 4). The purity of WT-ADI was further enhanced using the Q column in 20% elution buffer (FIG. 10, lane 7). The purified WT-ADI had a yield of about 16 mg/L cell, which accounted for about 88% recovery (Table 2). Its specific activity was 28.7 U/mg (Table 2). The molecular mass of WT-ADI detected by Liquid Chromatography-Electrospray Ionization Mass Spectrometry (LC-ESI-MS) was measured as 46377 Da (calculated mass=46376 Da), which had a proton attached on the protein (FIG. 1*a*). The two mutants were purified by the same method as WT-ADI. The specific activity of 44C and 265C was 16.0 and 19.4 U/mg, respectively (Table 2). The measured mass values of 44C (FIG. 11A) and 265C (FIG. 1B) was 46365 and 46362 Da, respectively.

TABLE 2

Purification table of wild type arginine deiminase (WT-ADI).

| Sample | Protein concentration (mg/ml) | Volume (ml) | Total protein (mg) | Specific activity (U/mg) | Total Activity (U) | Recovery (%) |
|---|---|---|---|---|---|---|
| Total lysate | 4.9 | 25 | 122.5 | — | — | — |
| Soluble fraction | 4.1 | 24.5 | 99.2 | 0.2 | 22 | — |
| Inclusion body | 6.2 | 5 | 30.9 | — | — | — |
| Before anion exchange column | 1.1 | 10 | 10.7 | 25.3 | 271 | 100 |
| WT-ADI | 6.1 | 1.4 | 8.3 | 28.7 | 238 | 88 |
| 44C | — | — | — | 16.0 | — | — |
| 265C | — | — | — | 19.4 | — | — |

Verification of the Attachment of Fluorescein-5-maleimide (F5M) on 44C and 265C

Figure 2:
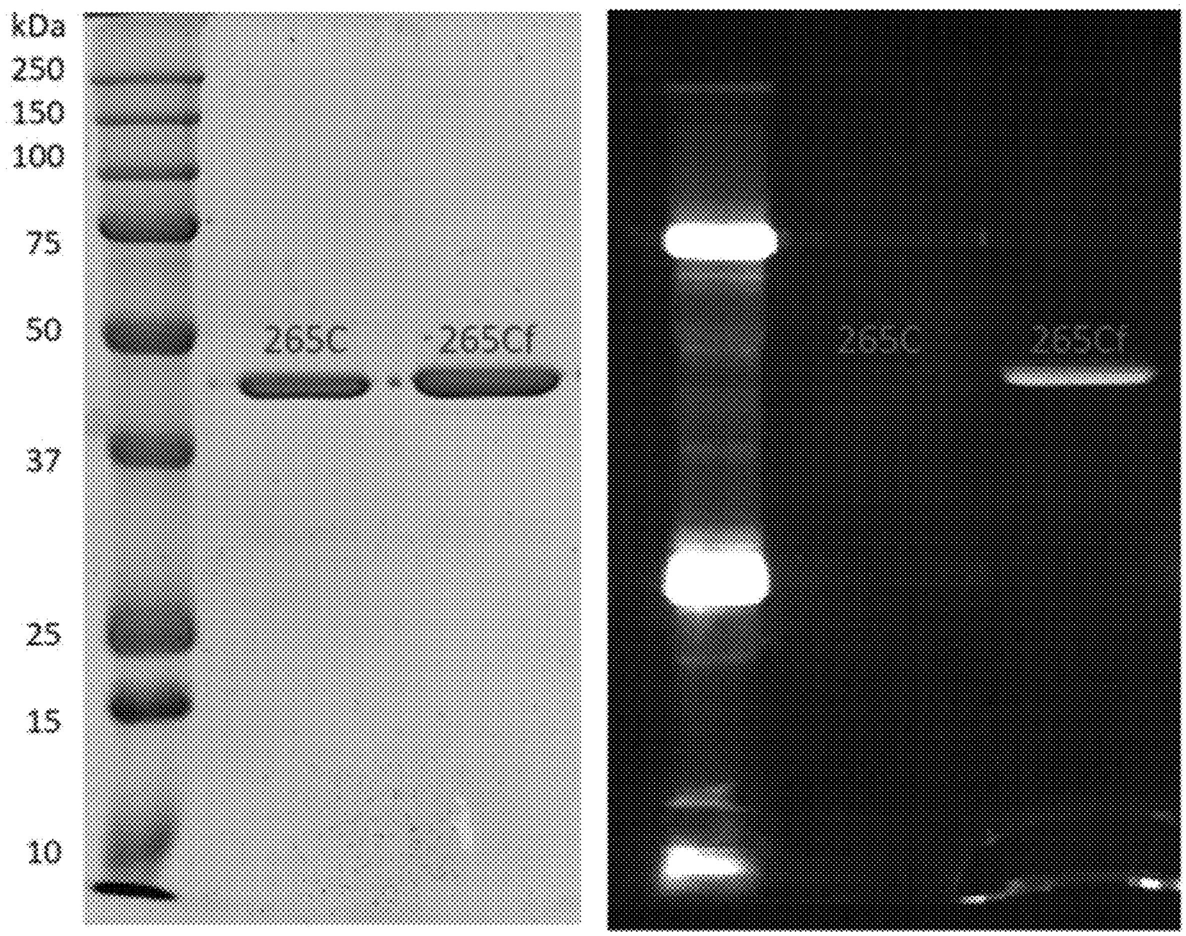
FIG. 2 depicts SDS-PAGE analysis of 265C before and after it was labelled with fluorescin-5-maleimide. (A) Staining with Coomassie Blue. (B) Exposure under ultraviolet light.

The purified 44C and 265C were labelled with F5M to become 44Cf and 265Cf, respectively. The ability to generate fluorescence of 44Cf and 265Cf was analysed by SDS-PAGE (FIG. 2 and). Before the labelling, 44C and 265C did not show any intrinsic fluorescence (FIG. 2). To confirm the complete labelling on them, the molecular mass values of 44Cf and 265Cf were verified by LC-ESI-MS measurements. The measured mass values of 44Cf and 265Cf were 46777 and 46789, respectively (FIG. 1*c*). Their mass differences before and after labelling were exactly 427 Da (corresponding to the mass of F5M) (FIGS. 1*b* and 1*c*), showing a single attachment of F5M on them. It was also found that 265C was completely labelled by F5M since a peak corresponding to the mass of 265C was absent from the spectrum of FIG. 1C. Unlike 265Cf, the peak corresponding to 44C was observed in FIG. 11B, showing its incomplete labelling by using the same method.

Figure 3:
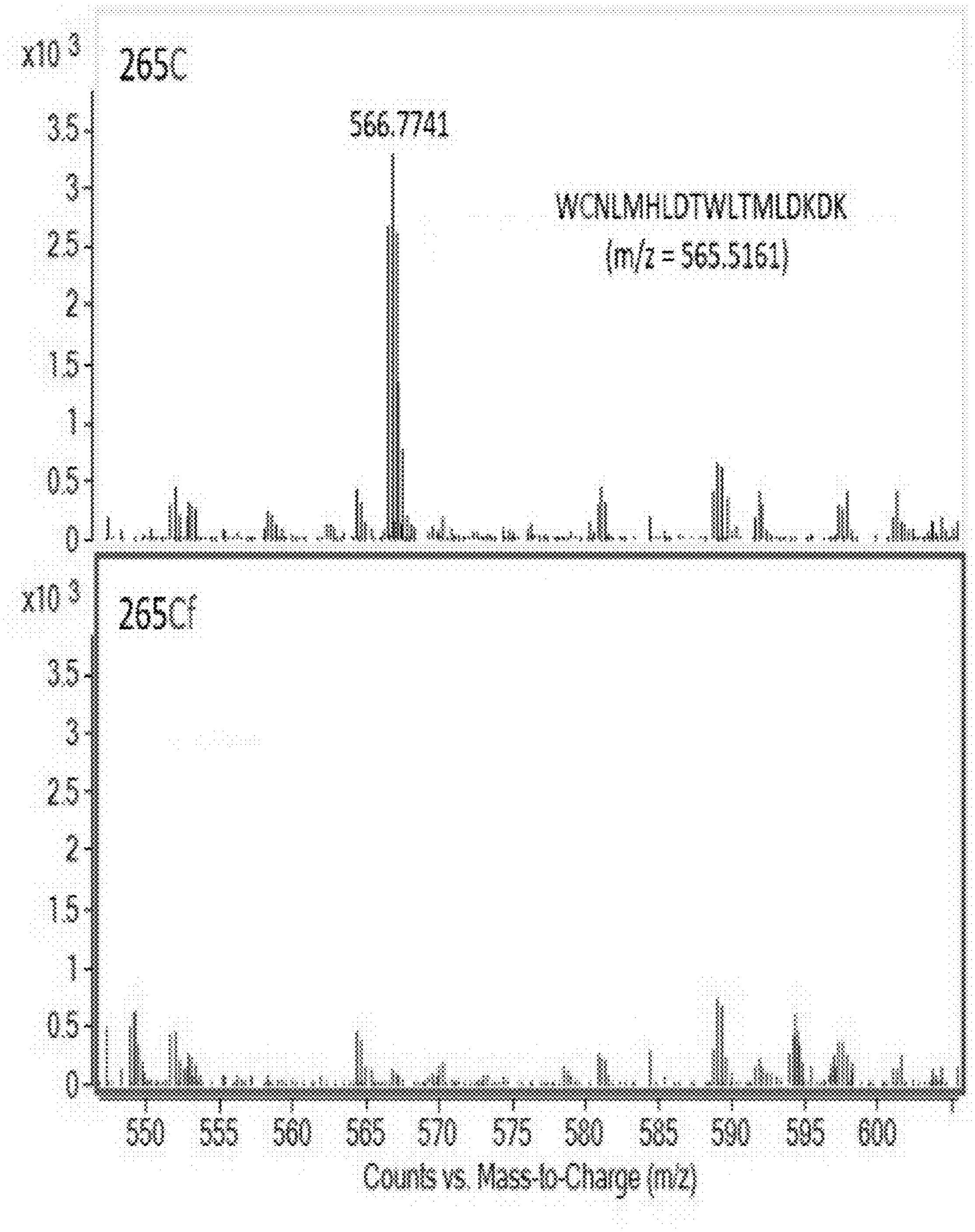
FIG. 3 depicts ESI-MS spectra of trypsin digested 265C and 265Cf. (A) A peptide fragment showing the amino acid sequence from the position of 264 to 281 (WCNLMHLDTWLTMLDKDK, Residues 264 to 281 of SEQ ID NO: 1) with a m/z value of 566.7741 present in 265C but not 265Cf (B) A peptide fragment showing the amino acid sequence from 264 to 281 (WCNLMHLDTWLTMLDKDK (Residues 264 to 281 of SEQ ID NO: 1)+fluorescein-5-maleimide (F5M)+water adduct) with a m/z value of 678.0437 only present in 265Cf but not in 265C.
Figure 3:
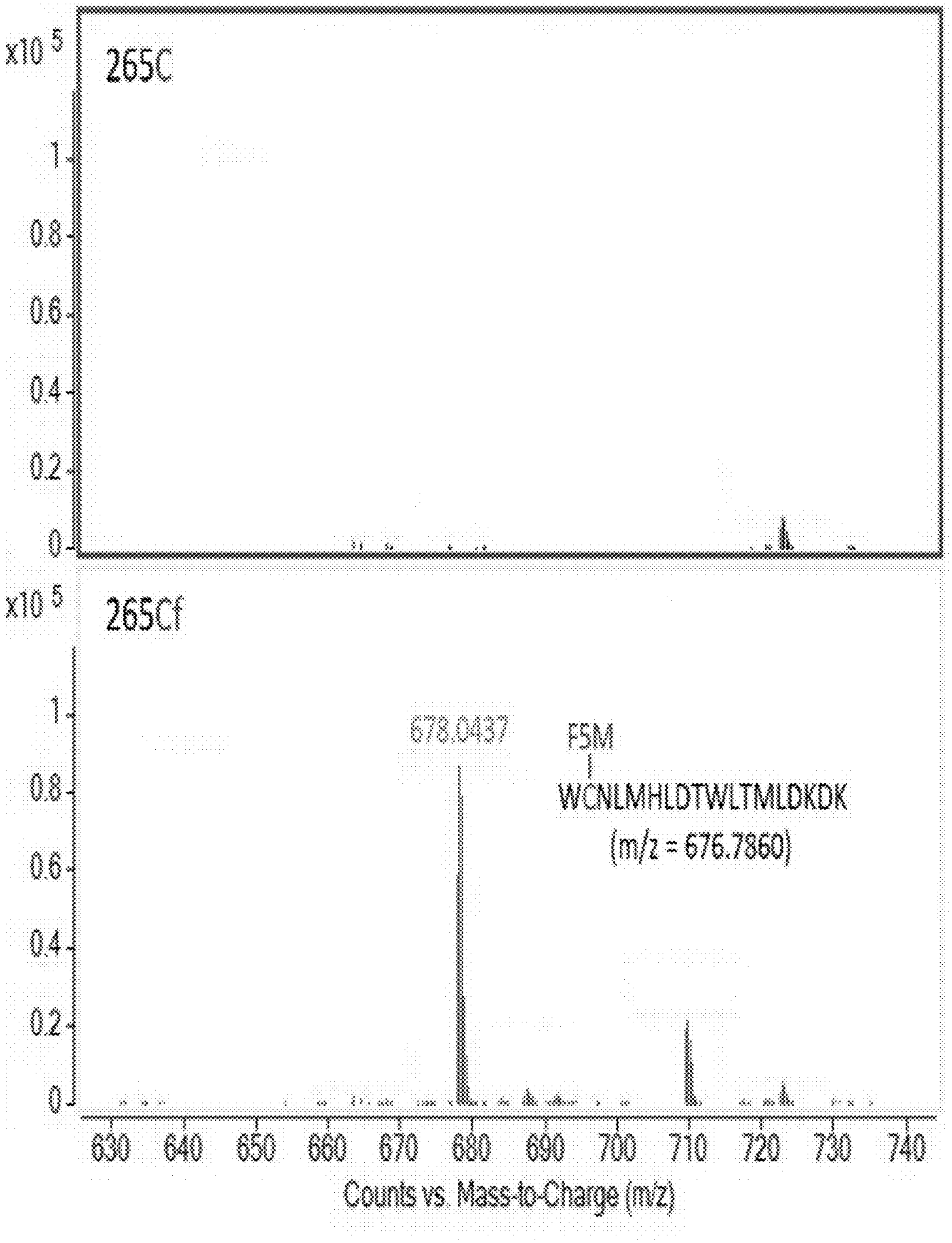
Figure 13:
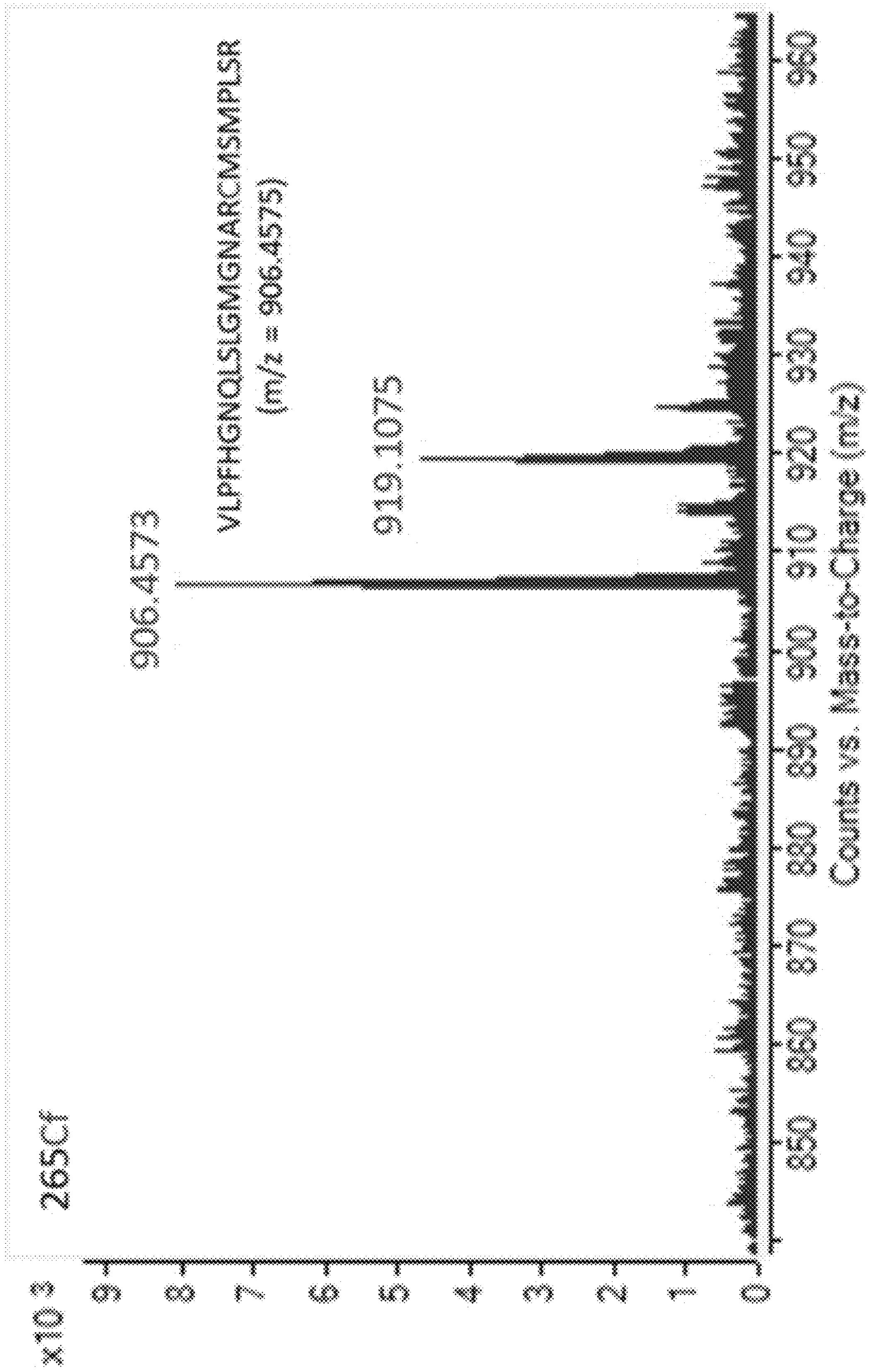
FIG. 13 depicts ESI-MS spectrum of trypsin digested 265Cf. A peptide fragment showing the amino acid sequence from the position of 381 to 405 (VLPF) with a m/z value of 906.4575 present in 265Cf.
Figure 14:
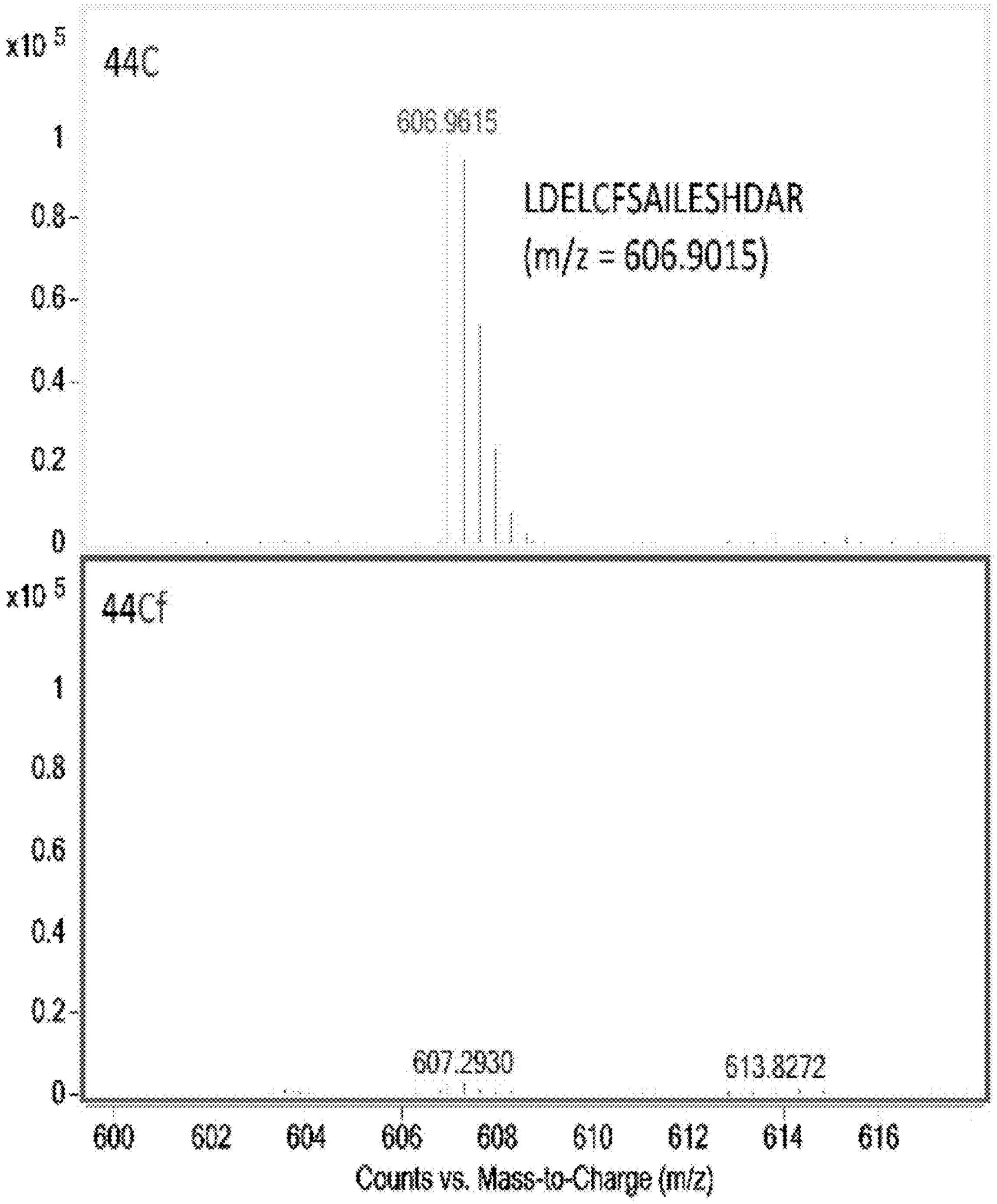
FIG. 14 depicts ESI-MS spectra of trypsin digested 44C and 44Cf. (A) A peptide fragment showing the amino acid sequence from the position of 40 to 55 (LDELCFSAILESHDAR, Residues 40 to 55 of SEQ ID NO: 2) with a m/z value of 606.9615 present in 44C but not 44Cf. (B) A peptide fragment showing the amino acid sequence from 40 to 55 (LDELCFSAILESHDAR (Residues 40 to 55 of SEQ ID NO: 2)+fluorescein-5-maleimide (F5M)+water adduct) with a m/z value of 755.3221 only present in 44Cf but not in 44C.
Figure 14:
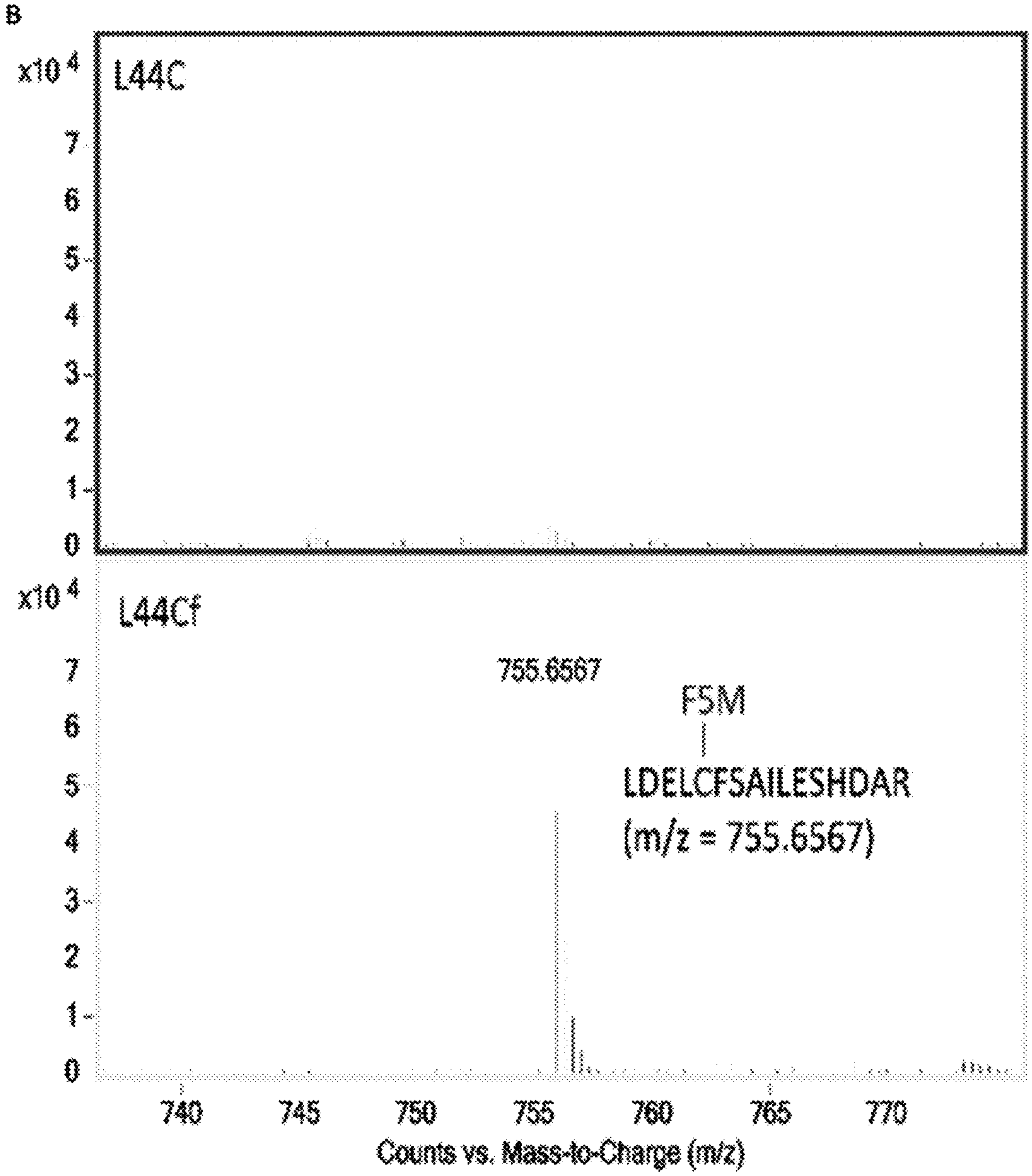

To ensure the site-specific attachment of F5M on designated $Cys^{44}$ and $Cys^{265}$, parallel trypsin digestions were done on mutants before and after labelling. Their digested peptide fragments were analysed by LC-ESI-MS. In the analysis of 265C and 265Cf, it was found that a peptide fragment (WCNLMHLDTWLTMLDKDK, Residues 264 to 281 of SEQ ID NO: 1) representing the amino acid sequence from the position of W264 to K281 with a mass to charge ratio (m/z) of 566.7741 was only found in 265C but not in 265Cf (FIG. 3A). On the other hand, a m/z value of 676.786 corresponding to the incorporation of that peptide segment and F5M was only present in 265Cf but not in 265C (FIG. 3B). These results proved the site-specific labelling of 265C by F5M. Furthermore, non-specific labelling on $Cys^{398}$ at the active site was not observed in 265Cf since a peptide segment (VLPFHGNQLSLGMGNARCMSMPLSR, Residues 381 to 405 of SEQ ID NO: 1) representing the amino acid sequence from the position of V381 to R405 without the attachment of F5M on its cysteine residue (m/z=906.457) could be detected in 265Cf (FIG. 13). On the other hand, the site-specific attachment o F5M on 44C was also confirmed by the presence of the peptide (LDELCFSAILESHDAR, Residues 40 to 55 of SEQ ID NO: 2) associated with F5M in the spectrum of 44Cf (FIG. 14).

Kinetic Parameters of Arginine Deiminases

The kinetic parameters of WT-ADI and two mutants before and after labelling with F5M were studies. There kinetic profiles were shown in FIGS. 4 and 15. The catalytic efficiency ($k_{cat}/K_m$) of WT-ADI, 265C and 44C was 988±272, 1025±311 and 138±52 $mM^{-1}s^{-1}$, respectively (Table inside FIGS. 4 and 15). The double mutations ($Cys^{251}$→$Ser^{251}$ and $Thr^{265}$→$Cys^{265}$) introduced on ADI conserved the catalytic efficiency as wild-type while the mutations on $Cys^{251}$→$Ser^{251}$ and $Leu^{44}\Delta Cys^{44}$ significantly lowered its catalytic efficiency, which was about a 7-fold decrease. The attachment of F5M did not alter their catalytic efficiencies (FIGS. 4 and S6).

Fluorescence Intensity of 44Cf and 265Cf in Phosphate-Buffered Saline (PBS) System 44Cf and 265Cf performed as 'turn-off' biosensors when reacting with L-Arg. Before the addition of L-Arg, their fluorescence remained at their baseline intensities (labelled as 0 μM L-Arg in figures) (FIGS. 5A and 5C). After the addition of L-Arg, the fluorescence intensities were quenched and restored to the baseline intensities upon the depletion of L-Arg (FIGS. 5A and 5C).

However, they acted differently in two ways. The first difference was the rates of restoring to the baseline intensities were varied, in which the 265Cf was faster than 44Cf (FIGS. 5A and 5C). The second difference was the percentage changes of fluorescence intensities against the concentrations of L-Arg. It was shown that the fluorescence intensity at time=0 decreased with respect to the increase of L-Arg concentration in 44Cf (FIG. 5A) whilst it remained at almost the same level when the concentration of L-Arg increased in 265Cf (FIG. 5C). When their percentages of fluorescence intensities changes were plotted against the concentration of L-Arg, it was shown that they did not have strong linear relationships (FIGS. 5B and 5D).

Figure 16:
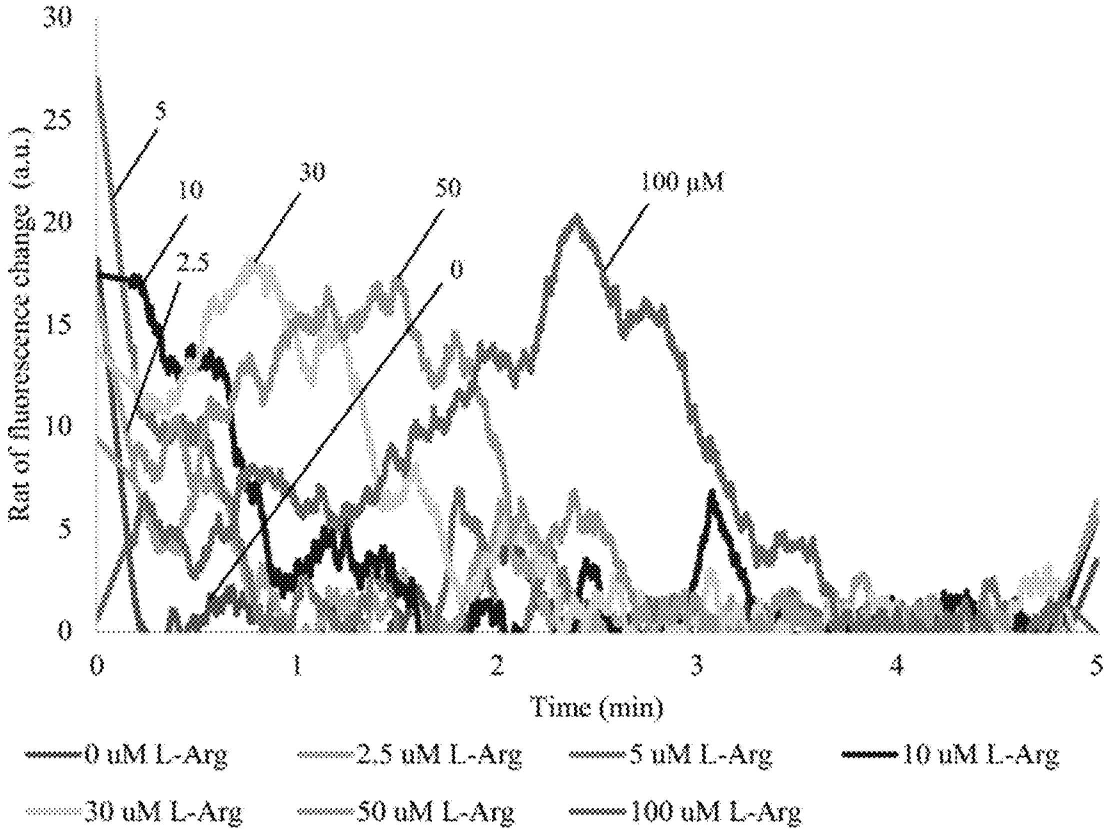
FIG. 16 depicts the rates of the fluorescence changes of 44Cf mixed with different concentrations of L-Arg.

It was interesting to note that the duration of fluorescence quenching changed with respect to the concentration of L-Arg in 265Cf (FIG. 6A). The higher the concentration of L-Arg was, the longer the time it would take for restoration of the fluorescence to the baseline intensity (labelled as 0 μM L-Arg in figures). Also, this quenching was specific to L-Arg, but not other amino acids, including asparagine, aspartic acid, agmatine, citrulline, glutamine, and glutamic acid (FIGS. 7A and 7B). Therefore, the time when the fluorescence changes occurred was used to correlate with L-Arg concentrations. The time was collected by finding the maximum rate of the fluorescence change (FIG. 6B). The relationship between the time at the maximum rate of the fluorescence change and the L-Arg concentration was linear with $R^2$=0.9988 (FIG. 6C). The linear detection range was 2.5-100 μM of L-Arg and the assay response time was 0.15-4 min (FIG. 6C). However, the time at the maximum rate of fluorescence change could not be well defined in 44Cf as in 265Cf (FIG. 16).

Application of 265Cf on the Detection of L-Arg in Fetal Bovine Serum

Since 265Cf showed its linear relationship with respect to the concentration of L-Arg, it was applied to the detection of L-Arg concentration in animal serum (e.g. fetal bovine serum) by using the standard addition method and without sample-pre-treatment. The pattern of fluorescence change in serum was similar to that in PBS system, in which the fluorescence intensity was suppressed in the presence of L-Arg and then returned back to the baseline intensity (FIG. 8A).

Although the fluorescence intensity changes were lower in serum in comparison to that in the calibration curve (FIGS. 6A, 8A, and S8A), the time at the maximum rate of the fluorescence change could still be defined (FIGS. 8B and S8B) and were linearly proportional to L-Arg concentration (FIGS. 8C and S8C). By using standard addition method, the L-Arg concentration in fetal bovine serum was measured as 47.2±6.0 μM by the first batch biosensor and as 48.9±1.2 μM by the second batch biosensor. These were in line with the result determined by mass spectrometry, which was 48.3±1.5 μM (Table 3). This application showed the simple use of 265Cf on the determination of L-Arg in complex systems, i.e. biological samples.

TABLE 3

The L-Arg concentration in fetal bovine serum analysed by 265Cf and mass spectrometry. Each batch of enzyme was performed in n = 3. Batch 1 and batch 2 are two different batches of production.

| | L-Arg concentration (μM) |
|---|---|
| 265Cf (Batch 1 in present study) | 47.2 ± 6.0 |
| 265Cf (Batch 2 in present study) | 48.9 ± 1.2 |
| Mass spectrometry | 48.3 ± 1.5 |

Molecular Modelling of 265Cf

The phenomenon on the fluorescence intensity changes induced by 265Cf in the presence of L-Arg was investigated by molecular modelling. We hypothesized that a residue $Trp^{264}$ adjacent to fluorescein-labelled cysteine could give rise to fluorescence quenching. To illustrate this, two models were manually built: the apo-protein (FIG. 9A) and the L-Arg-complexed protein (FIG. 9B). In the apo-protein, the fluorescein moiety on $Cys^{265}$ was remote from $Trp^{264}$ while residue $Met^{393}$ occupied part of the empty active site (FIG. 9A). From our apo protein model, this distance was measured to be 10.8 Å (FIG. 9A). In the presence of L-Arg, $Met^{393}$ was pushed outward which caused the fluorescein moiety to move closer by approximately 5 Å to $Trp^{264}$ and its fluorescence was thus quenched (FIG. 9B). From our complexed model, this distance was now 6.0 Å (FIG. 9B).

Figure 18:
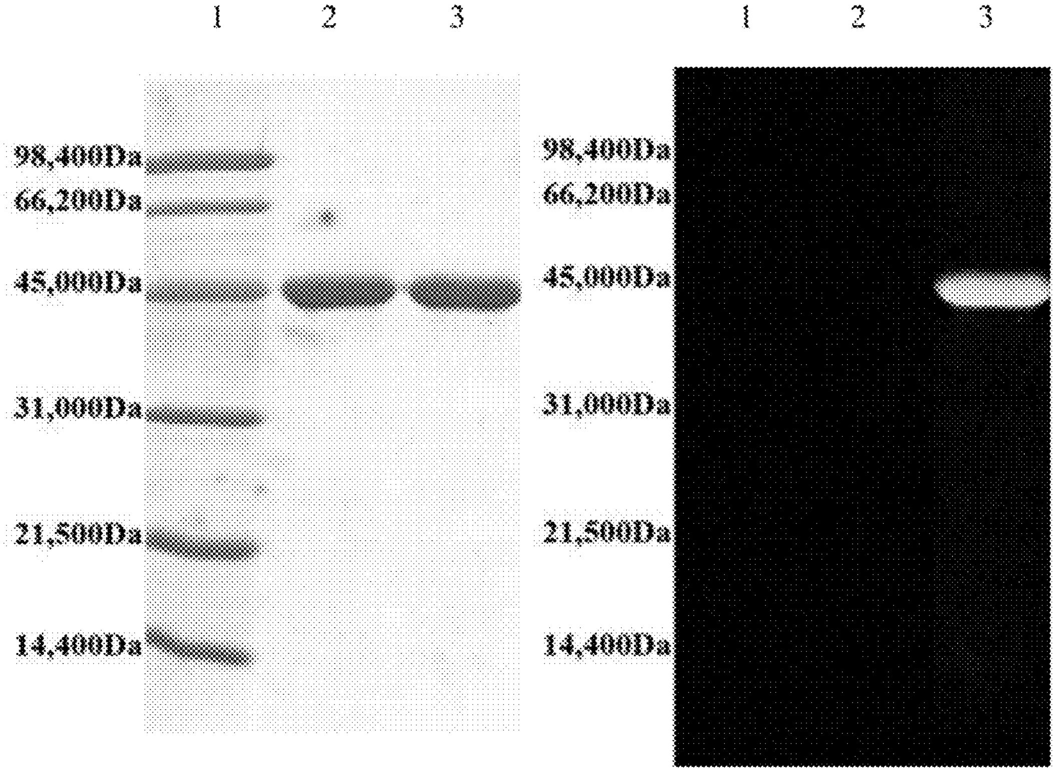
FIG. 18 depicts SDS-PAGE analysis of wild-type ADI and the 44C mutant of ADI. Both enzymes were subjected to the same fluorophore labeling with fluorescein-5-maleimide. On the Left, the SDS-PAGE gel shows the protein makers (lane 1), wild-type ADI (lane 2), and the 44C mutant of ADI (lane 3). On the Right, the SDS-PAGE gel shows the wild-type enzyme with no fluorescent band (lane 2), whereas the 44C mutant gives a strong fluorescent band (lane 3).

Sensing Properties of the Fluorescein-Labeled and Badan-Labeled 44C Mutant of the *Mycoplasma arginini* ADI For the 44C mutant of *M. arginini* ADI, the $Cys^{44}$ residue can be labeled with the thiol-reactive fluorophore fluorescein-5-maleimide. In one experiment, we investigated whether fluorescein-5-maleimide is specifically attached to the $Cys^{44}$ residue in the mutant. To this end, we performed the labeling reaction of fluorescein-5-maleimide with both wild-type ADI and the 44C mutant and then analyzed the fluorophore labeling results by SDS-PAGE. As shown in FIG. 18, wild-type ADI does not show a fluorescent band, whereas the 44C mutant gives a green fluorescent band. These observations indicate that thiol-reactive fluorescein-5-maleimide is specifically linked to the $Cys^{44}$ residue.

Figure 19:
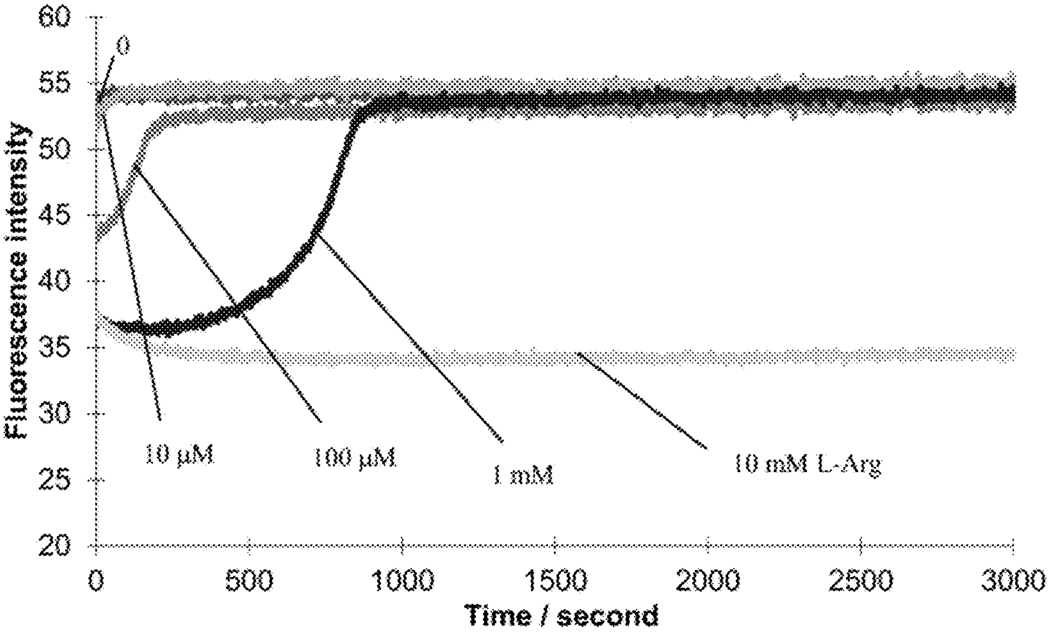
FIG. 19 depicts time-course fluorescence measurements of the fluorescein-labeled 44C mutant of ADI with different concentrations of L-Arg. L-Arg concentration=0 M, 10 μM, 100 μM, 1 mM, and 10 mM. Concentration of Fluorescein-labeled 44C=0.25 μM. Buffer: 50 mM potassium phosphate buffer (pH 6.4).
Figure 20:
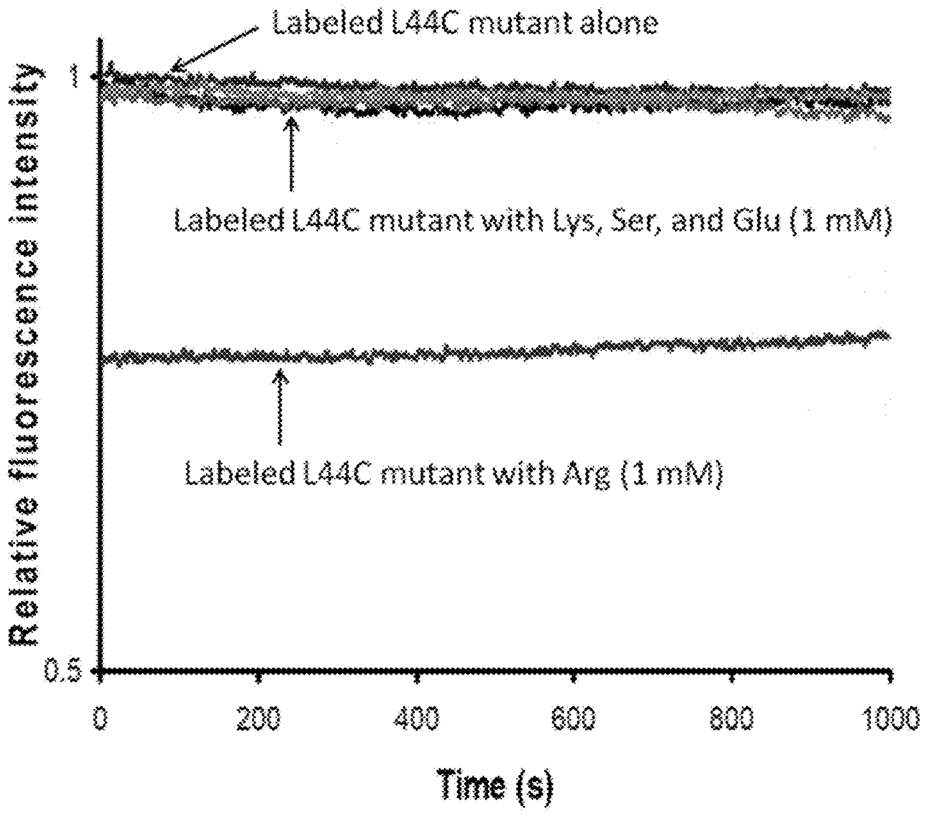
FIG. 20 depicts time-course fluorescence measurements of the fluorescein-labeled 44C mutant of ADI with and without different amino acids. Fluorescein-labeled 44C mutant alone; fluorescein-labeled 44C mutant with lysine, serine, glutamic acid, and arginine. Concentration of amino acid=1 mM. Buffer: 50 mM potassium phosphate buffer (pH 6.4).

We then investigated the ability of the fluorescein-labeled 44C mutant to detect L-Arg. We performed time-course fluorescence measurements on the fluorescein-labeled 44C mutant with different concentrations of L-Arg. Without L-Arg, the fluorescein-labeled 44C mutant gives steady fluorescence over the time course (FIG. 19). Interestingly, upon addition of L-Arg, the fluorescence of the fluorescein-labeled 44C mutant declines instantaneously and then increases gradually to its original level over the time course (FIG. 19). The fluorescence quenching on the fluorescein-labeled 44C mutant is stronger when L-Arg is present at higher concentration (0-10 mM) (FIG. 19). This characteristic fluorescence response is presumably due to the fluorescence quenching effect of the L-Arg bound to the active site. After catalytic reaction, the fluorescein-labeled 44C mutant appears to be regenerated as free enzyme, thus restoring its original fluorescence (FIG. 19). The fluorescein-labeled 44C mutant can recognize L-Arg with high specificity, as revealed by the fluorescence profiles that only L-Arg can significantly quench the fluorescence of the labeled mutant, whereas "non-binders" (e.g. lysine, glutamic acid, and serine) do not significantly change the fluorescence of the labeled mutant (FIG. 20). It is worth noting that the fluorescein-labeled 44C mutant can detect 100 μM L-Arg, which is a common concentration level for L-Arg in human blood (FIG. 19).

Figure 21:
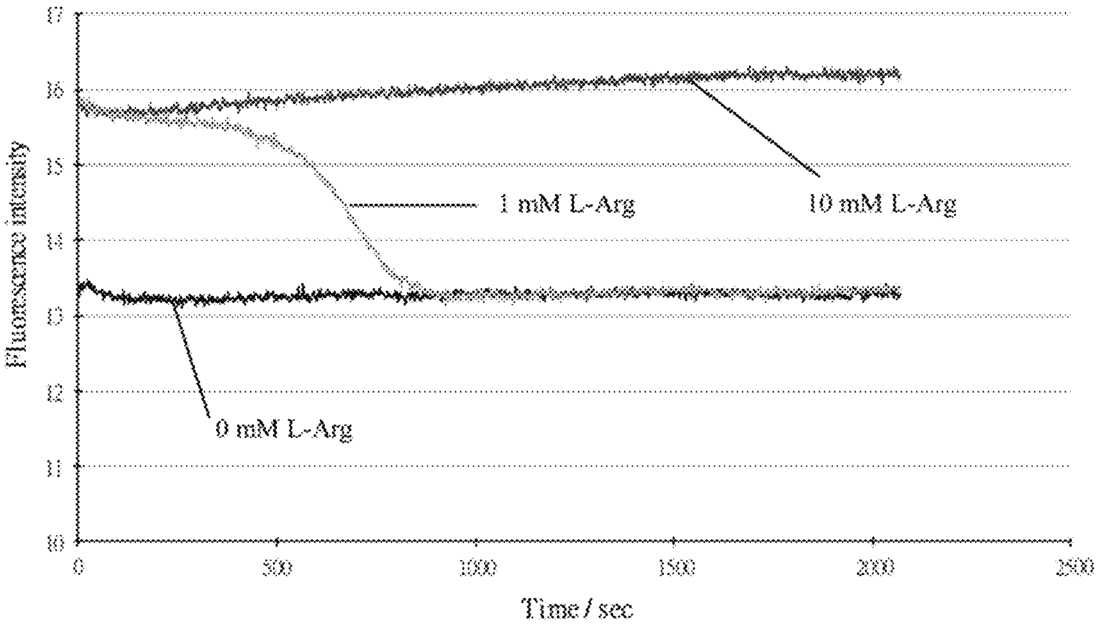
FIG. 21 depicts time-course fluorescence measurements of the badan-labeled 44C mutant of ADI with different concentrations of L-Arg. Concentration of $_{L\text{-}Arg}$=0 mM, 1 mM, and 10 mM. Concentration of Badan-labeled 44C=0.25 μM. Buffer: 50 mM potassium phosphate buffer (pH 6.4).

We also labeled the 44C mutant with another environment-sensitive fluorophore (badan) and did time-course fluorescence measurements with L-Arg. We found that the badan-labeled 44C mutant gives stronger fluorescence upon addition of L-Arg (1 mM) and then restores its weak fluorescence after 900 seconds (FIG. 21). This observation is presumably due to the fact that the badan label experiences a "hydrophobic" environment upon L-Arg binding and then a "polar" environment after the enzymatic reaction on L-Arg and the subsequent release of the product from the active site. With 10 mM L-Arg, the badan-labeled 44C mutant is likely to be saturated, thus giving sustained strong fluorescence over the time course (FIG. 21). The stronger fluorescence of badan towards L-Arg binding indicates that it is a "turn-on" fluorescent biosensor rather than a "turn-off" biosensor.

Fluorophore labeling of the 44C mutant: For fluorescein-5-maleimide labeling, the 44C mutant (1 mg/mL) was mixed with a 10-fold molar excess of fluorescein-5-maleimide (20 mM, dissolved in DMF) and stirred at 400 rpm at room temperature for 2 hours under a dark condition. The fluorescein-labeled mutant was then dialyzed with a dialysis bag (MWCO=3,000 Da) against deionized $H_2O$ (4 L) at 4° C. to remove excess fluorescein. The fluorescein-labeled mutants were analyzed by SDS-PAGE and electrospray ionization mass spectrometry (ESI-MS) to check the extent of fluorophore labeling. On the other hand, for badan labeling, the 44C mutant (1 mg/mL) was dissolved in 2 M guanidine HCl (in 50 mM potassium phosphate, pH 7.5). A 10-fold molar excess of badan (20 mM, dissolved in DMF) was added to the protein solution, and the protein sample was stirred at room temperature for 2 h under a dark condition. The badan-labeled mutant was then dialyzed using a dialysis bag (MWCO=3,000 Da) against deionized $H_2O$ (4 L) at 4° C. to remove excess badan. The badan-labeled mutant was analyzed by SDS-PAGE and electrospray ionization mass spectrometry (ESI-MS) to check the extent of fluorophore labeling.

Fluorescence studies of the 44C mutant: To investigate the fluorescence responses of the fluorescent ADI mutant towards substrate (L-Arg) binding, time-course fluorescence measurements were performed on the fluorescein-labeled mutant of ADI (0.25 μM) with different concentrations of substrate (0-10 mM L-Arg) in 50 mM potassium phosphate buffer (pH 6.4). Using the spectrofluorometer (Perkin-Elmer, model LS50B), the fluorescein label on the ADI mutant was excited at a wavelength of 494 nm, and its fluorescence at a wavelength of 515 nm was monitored as a function of time. Similar time-course fluorescence studies were also performed on the badan-labeled mutant of ADI. The fluorescence data (FIG. 19) show that the fluorescence decrease of the labeled 44C mutant is dependent on the concentration of L-Arg; the higher the concentration of L-Arg, the lower the fluorescence signal of the labeled 44C mutant (FIG. 19).

What is claimed is:

1. A fluorescent recombinant arginine deiminase (ADI) comprising a recombinant ADI comprising a polypeptide having an amino acid sequence that is at least 95% identical to SEQ ID NO: 1 or SEQ ID NO: 2, wherein the amino acid at position 251 of SEQ ID NO: 1 is not cysteine while the amino acid at position 265 of SEQ ID NO: 1 must be cysteine; and the amino acid at position 44 of SEQ ID NO: 2 must be cysteine while the amino acid at position 251 of SEQ ID NO: 2 is not cysteine, and a fluorescent dye covalently attached via an optional linker to the side chain of the cysteine at position 265 of SEQ ID NO: 1 or to the side chain of the cysteine at position 44 of SEQ ID NO: 2.

2. The fluorescent recombinant ADI of claim 1, wherein the amino acid at position 251 of SEQ ID NO: 1 must be serine; and the amino acid at position 251 of SEQ ID NO: 2 must be serine.

3. The fluorescent recombinant ADI of claim 1, wherein the polypeptide has an amino acid sequence that is at least 97.5% identical to SEQ ID NO: 1 or SEQ ID NO: 2.

4. The fluorescent recombinant ADI of claim 1, wherein the polypeptide has an amino acid sequence that is at least 98.7% identical to SEQ ID NO: 1 or SEQ ID NO: 2.

5. The fluorescent recombinant ADI of claim 1, wherein the recombinant ADI consists of SEQ ID NO: 1 or SEQ ID NO: 2.

6. The fluorescent recombinant ADI of claim 1, wherein the fluorescent dye comprises a fluorescein derivative, a BODIPY derivative, an eosin derivative, a rhodamine derivative, a PyMPO derivative, a benzoxadiazole derivative, or a Lucifer yellow derivative.

7. The fluorescent recombinant ADI of claim 6, wherein the fluorescent dye is attached via a linker comprising a 2,5-dioxopyrrolidin-3-yl moiety, an acetyl moiety, or an ethylene moiety to the side chain of the cysteine at position 265 of SEQ ID NO: 1 or to the side chain of the cysteine at position 44 of SEQ ID NO: 2.

8. The fluorescent recombinant ADI of claim 1, wherein the fluorescent dye and linker is fluorescein-5-(2,5-dioxopyrrolidin-3-yl).

9. A method of detecting L-arginine (L-Arg) in a sample suspected of containing L-Arg, the method comprising: contacting the fluorescent recombinant ADI of claim 1 with the sample and measuring the fluorescence of the fluorescent recombinant ADI.

10. The method of claim 9, wherein the fluorescent recombinant ADI consists of SEQ ID NO: 1 or SEQ ID NO: 2.

11. The method of claim 9, wherein the fluorescent dye is a fluorescein derivative, a BODIPY derivative, an eosin derivative, a rhodamine derivative, a PyMPO derivative, a benzoxadiazole derivative, or a Lucifer yellow derivative; and the fluorescent dye is attached via a linker comprising a N-succinimidyl (2,5-dioxopyrrolidin-3-yl) moiety, an acetyl moiety, or an ethylene moiety to linker to the side chain of the cysteine at position 265 of SEQ ID NO: 1 or to the side chain of the cysteine at position 44 of SEQ ID NO: 2.

12. The method of claim 9, wherein the fluorescent dye and linker is fluorescein-5-N-succinimidyl, 6-acetamidofluorescein (6-iaf), tetramethylrhodamine-5-N-succinimidyl (T5M), or 6-acetyl-2-dimethylaminonaphthalene (BADAN).

13. The method of claim 9 further comprising the step of determining the concentration of L-Arg in the sample based on the measured fluorescence of the fluorescent recombinant ADI.

14. The method of claim 13, wherein the step of measuring the fluorescence of the fluorescent recombinant ADI comprises measuring the time at the maximum rate of the fluorescence change of the fluorescent recombinant ADI in the sample.

15. The method of claim 14, wherein the step of determining the concentration of L-Arg in the sample comprises comparing the measured time at the maximum rate of the fluorescence change of the fluorescent recombinant ADI in the sample to one or more calibration curves prepared by using the interrelation between known concentrations of L-Arg in standard samples comprising the fluorescent recombinant ADI and the time at the maximum rate of the fluorescence change of the fluorescent recombinant ADI in the standard samples; and determining the concentration of L-Arg in the sample.

16. The method of claim 9, wherein the method has a linear detection range of 2.5 to 100 μM L-Arg in the sample.

17. The method of claim 9, wherein the time required from the step of contacting the recombinant ADI and the sample to measuring the fluorescence of the recombinant ADI is between 0.15-4 minutes.

18. The method of claim 9, wherein the sample is a biological sample.

19. A method of preparing the fluorescent recombinant ADI of claim 1 the method comprising: contacting the recombinant ADI with a reactive fluorescent dye reagent comprising the fluorescent dye covalently bonded via an optional linker to a reactive moiety selected from the group consisting of maleimide moiety, an acetyl halide, and an ethylene halide thereby forming the fluorescent recombinant ADI.

20. The method of claim 19, wherein the reactive fluorescent dye reagent is fluorescein-5-maleimide, 6-iodoacetamidofluorescein (6-iaf), tetramethylrhodamine-5-maleimide (T5M), or 6-bromoacetyl-2-dimethylaminonaphthalene (BADAN).

* * * * *